(12) United States Patent
Ellis-Davies et al.

(10) Patent No.: US 7,897,638 B2
(45) Date of Patent: Mar. 1, 2011

(54) SYNTHESIS OF NITRODIBENZYLFURAN CHROMOPHORE FOR PHOTODEPROTECTION OF ORGANIC MOLECULES

(75) Inventors: Graham Ellis-Davies, Philadelphia, PA (US); Atsuya Momotake, Tsukuba (JP)

(73) Assignee: Philadelphia Health & Education Corporation, Philadelphia, PA (US)

( * ) Notice: Subject to any disclaimer, the term of this patent is extended or adjusted under 35 U.S.C. 154(b) by 543 days.

(21) Appl. No.: 11/911,250

(22) PCT Filed: Apr. 12, 2006

(86) PCT No.: PCT/US2006/013634
§ 371 (c)(1),
(2), (4) Date: Oct. 11, 2007

(87) PCT Pub. No.: WO2006/110804
PCT Pub. Date: Oct. 19, 2006

(65) Prior Publication Data
US 2008/0188645 A1      Aug. 7, 2008

Related U.S. Application Data

(60) Provisional application No. 60/670,435, filed on Apr. 12, 2005, provisional application No. 60/679,772, filed on May 11, 2005.

(51) Int. Cl.
*A61K 31/407* (2006.01)
*A61K 31/343* (2006.01)
*C07D 491/048* (2006.01)
*C07D 307/91* (2006.01)

(52) U.S. Cl. ................... 514/468; 514/410; 548/421; 549/460; 549/461

(58) Field of Classification Search ............... 514/468, 514/410; 548/421; 549/460, 461
See application file for complete search history.

(56) References Cited

U.S. PATENT DOCUMENTS

| | | |
|---|---|---|
| 4,981,985 A | 1/1991 | Kaplan et al. |
| 5,034,613 A | 7/1991 | Denk et al. |
| 5,430,175 A | 7/1995 | Hess et al. |
| 5,446,186 A | 8/1995 | Ellis-Davies et al. |
| 5,498,765 A | 3/1996 | Carpenter et al. |

(Continued)

FOREIGN PATENT DOCUMENTS

WO   WO2004085394 A1   10/2004

OTHER PUBLICATIONS

Keumi et al. J. Org. Chem. 1991, 56, 4671-4677.*

(Continued)

*Primary Examiner*—Joseph R. Kosack
*Assistant Examiner*—Matthew P Coughlin
(74) *Attorney, Agent, or Firm*—Caesar, Rivise, Bernstein, Cohen & Pokotilow, Ltd.

(57) ABSTRACT

Inventors have developed a chromophore (nitrodibenzylfuranyl, or NBDF) for ultra efficient uncaging of a caged substrate (e.g., an organic molecule such as, for example, an amino acid, a biological molecules, such as, for example, second messengers inside cells). Photolysis of a NBDF derivative of EGTA (i.e. caged calcium) is about 50 times more efficient than others calcium cages (the quantum yield of photolysis is 0.6 and the extinction coefficient is 18,400. NDBF-EGTA has a 2-photon cross section of about 0.3-0.6 GM).

6 Claims, 5 Drawing Sheets

U.S. PATENT DOCUMENTS 5,587,509 A    12/1996    Hess et al.

OTHER PUBLICATIONS

Merriam-Webster Online Dictionary entry for "derivative", (http://www.merriam-webster.com/dictionary/derivative), last accessed May 12, 2010.*

Momotake et al. Nature Methods, 2006, 3, 35-40.*

Kaplan, J. H. (1990) Annu. Rev. Physiol. 52, 897-914.

Adams, S. R., Kao, J. P. Y., Grynkiewicz, G., Minta, A., & Tsien, R. Y. (1988) J. Am. Chem. Soc. 110, 3212-3220.

Keumi, T., J. Org. Chem. (1991) vol. 56, pp. 4671-4677.

Wieboldt, R., Gee, K.Y., Niu, L., Ramash, D., Carpenter, B.K., and Hess, G.P. (1994b) "Photolabile presurors of glutamate: Synthesis, photochemical properties, activation of glutamate receptors in the microsecond time scale."Proc. Natl. Acad. Sci. (USA) (1994) vol. 91, pp. 8752-8756).

Patchornik A., J. Am. Chem. Soc. (1970) vol. 92, pp. 6333-6335).

Jasuja, et al., Biophysical Journal (1999) vol. 76, pp. 1706-1719.

Brewster, Organic Syntheses Collected vol. 2. pp. 445-446.

Ellis-Davies G.C.R. , (2005) in Imaging in Neuroscience and Development (Eds.: R. Yuste, A. Konnerth), Cold Spring Harbor Laboratory Press, Cold Spring Harbor, 2005, 367-374.

Corrie, J.E.T. et al., (1993) "Caged nucleotides and neurotransmitters" In Bioorganic Photochemistry 2 (ed. H. Morrison) John Wiley and Son, New York, pp. 243-305.

Corrie J.E.T., (2005) "Photoremovable Protecting Groups Used for the Caging of Biomolecules" in Dynamic Studies in Biology (eds Maurice Goeldner (Editor), Richard Givens) Wiley.

Ellis-Davies G.C.R et al., (1994) "Nitrophenyl-EGTA, a photolabile chelator that selectively binds Ca2+ with high affinity and releases it rapidly upon photolysis" Proc. Natl. Acad. Sci. USA, 91: 187-191.

Ellis-Davies G.C.R et al., A new class of photolabile chelators for the rapid release of divalent cations: generation of caged Ca and caged Mg. J. Org. Chem. 53 (1988) 1966-1969.

Kaplan et al., Photolabile chelators for the rapid photorelease of divalent cations Proc. Natl. Acda. Sci. (USA) 85 (1988) 6571-6575.

Ellis-Davies G.C.R, Synthesis of photolabile EGTA derivatives. Tetrahedron Lett. 39 (1998) 953-957.

Matsuzaki M. et al., Dendritic spine morphology is critical for AMPA receptor expression in hippocampal CA1 pyramidal neurons, Nature Neuroscience 2001, 4, 1086-1092.

Adams S.R. et al., A new caged Ca2+, azid-1, is far more photosensitive than nitrobenzyl-based chelators. Chem & Biol. 4 (1997) 867-878.

Tsien R.Y. et al., Control of cytoplasmic calcium with photoabile tetracaroxylate 2-nitrobenhydrol chelators. Biophys. J. 50 (1986) 843-853.

Adams S.R. et al., Biologically useful chelators that release Ca2+ upon illumination. J. Am. Chem. Soc. 110 (1998) 3212-3220.

Kantevari S. et al., Synthesis and 2-photon photolysis of 6-(ortho-nitroveratryl)-caged IP3, ChemBioChem. 2006, 7, 174-182.

Engert F et al., A low cost UV laser for flash photolysis of caged compounds, J. Neurosci. Methods. 1996 66, 47-54.

Engels J. et al., Synthesis, structure and reactivity of adenosine cyclic 3',5'-phosphate benzyl triesters, J. Med. Chem. 20, 907-911 (1977).

Kishimoto T. et al., Ion selectivities of the Ca2+ sensors for exocytosis in rat phaeochromocytoma cells., J. Physiol. 2001, 533, 627-637.

Delprincipe F. et al., Two-photon and UV-laser Flash Photolysis of the Ca2+ Cage, Dimethoxynitrophenyl-EGTA-4., Cell Calcium 1999, 25, 85-95.

Lipp P. et al., Fundamental calcium release events revealed by two-photon photolysis of caged calcium in guinea-pig cardiac myocytes., J. Physiol. 508 801-809 (1998).

Denk et al., Two-photon laser scanning fluorescence microscopy. Science 248, 73-76 (1990).

Denk, Two-photon scanning photochemical microscopy: mapping ligand-gated ion channel distributions., Proc. Natl. Acad. Sci. U. S. A. 1994, 91: 6629-6633.

Denk et al., Photo upmanship: why multiphoton imaging is more than a gimmick. Neuron 18, 351-357 (1997).

International Search Report for PCT/US2006/013634, 2006.

* cited by examiner

SYNTHESIS OF NITRODIBENZYLFURAN CHROMOPHORE FOR PHOTODEPROTECTION OF ORGANIC MOLECULES

CROSS-REFERENCE TO RELATED APPLICATIONS

This application claims the benefit of provisional Application No. 60/670,435, filed Apr. 12, 2005, titled SYNTHESIS OF NITRODIBENZYLFURAN CHROMOPHORE FOR PHOTODEPROTECTION OF ORGANIC MOLECULES and provisional Application No. 60/679,772, filed May 11, 2005, titled SYNTHESIS OF NITRODIBENZYLFURAN CHROMOPHORE FOR PHOTODEPROTECTION OF ORGANIC MOLECULES which are incorporated herein in its entirety.

STATEMENT REGARDING FEDERALLY SPONSORED RESEARCH OR DEVELOPMENT

This research was supported in part by U.S. Government funds (National Institute of Health, Grant No. GM53395), and the U.S. Government may therefore have certain rights in the invention.

BACKGROUND OF THE INVENTION

1. Field of Invention

This invention relates to photochemical protecting groups or chromophores and more specifically it relates to photorelease of effector molecules by photoreleasing caged compounds.

2. Description of Related Art

Light is an essential tool for studying cells. High photonic fluxes are often required to acquire a distinct signal in fluorescence microcopy, but such high power can also disrupt cells (by heating, singlet oxygen production, etc.), and bleach endo/exogenous chromophores. Photolabile "caged" compounds are inert precursors of bioactive molecules that can be loaded into cells and later released in their active form. Photochemical uncaging of biological signaling molecules typically uses brief bursts of light (near-UV wavelengths for regular, one-photon uncaging, or near-IR light for 2-photon photolysis). This mechanism is highly advantageous in studying the kinetics of important signaling events such as, for example, activation of receptors and ion channels and release of neurotransmitters.

Ionized calcium ($Ca^{2+}$) is an important second messenger for a wide variety of physiological and biochemical processes such as muscle contraction, neurotransmitter release, ion channel gating, exocytosis, etc. The essential role of $Ca^{2+}$ release and sequestration in intracellular communication has also been recently highlighted by the growing appreciation of the importance of inositol phospholipid metabolism in signaling. A technique for the controlled, localized, and rapid increase in $[Ca^{2+}]$ would provide a tool which would enable the study of the kinetic, regulatory, and structural mechanisms of such processes. Two approaches to this problem have been taken (see Kaplan, J. H. (1990) Annu. Rev. Physiol. 52, 897-914). The first, developed by Tsien and co-workers, involves reducing the $Ca^{2+}$-buffering capacity of a BAPTA derivative by decreasing the electron donating capacity of one of the coordinating ligands on illumination following the photoexpulsion of a small molecule from the chelator. This strategy has led to two readily available photosensitive buffers, nitr-5 and nitr-7 (Adams, S. R., Kao, J. P. Y., Grynkiewicz, G., Minta, A., & Tsien, R. Y. (1988) J. Am. Chem. Soc. 110, 3212-3220).

Changes in $Ca^{2+}$ signaling are observed in various human pathologies such as, for example cancer and neurodegenerative diseases. It has been shown that the spatio-temporal characteristics of $Ca^{2+}$ signals can regulate the activity of transcription factors and directly affect gene expression.

U.S. Pat. No. 5,446,186 to Ellis-Davies et al. describes an approach to caging $Ca^{2+}$ and is directed to photosensitive derivatives of chelators with known high affinity for $Ca^{2+}$, which upon illumination were bifurcated, producing two moieties with known low affinity, thus the bound $Ca^{2+}$ was released. U.S. Pat. No. 5,446,186 describes a photosensitive $Ca^{2+}$ chelator, called nitrophenyl-EGTA (NP-EGTA) that binds $Ca^{2+}$ selectively with high affinity (80 nM), which upon photolysis is bifurcated producing iminodiacetic acid photoproducts with a 12,500-fold lower affinity for $Ca^{2+}$. This compound possesses the desired properties of $Ca^{2+}$ selectivity in combination with a rapid high photochemical yield of liberated $Ca^{2+}$.

DM-nitrophen (U.S. Pat. No. 4,981,985) is a commercially available photosensitive derivative of EDTA has found wide application during the last several years as a photolabile chelator of divalent cations, particularly as caged $Ca^{2+}$ and caged $Mg^{2+}$. The distinct advantage of nitr-5 and nitr-7 compared to DM-nitrophen is that they are $Ca^{2+}$-selective chelators whereas DM-nitrophen has chelation properties similar to EDTA. The comparative advantages of DM-nitrophen are that its $Ca^{2+}$ affinity is very high before photolysis and very low after photolysis, thus ensuring a good photochemical yield of liberated $Ca^{2+}$.

U.S. Pat. No. 4,981,985 to Ellis-Davies et al. discloses the synthesis of photolabile chelators for multivalent cations and the method of synthesizing photolabile chelators as EDTA and EGTA derivatives to be used in caging multivalent cations. The molecules chelate the cations forming non-biologically active compounds. Upon irradiation, the chelated cation cleaves with the subsequent cleaved remainders having a substantially lower affinity for the chelated divalent cation. Large amounts of cations are thus rapidly released and the effect of such concentration jumps on the biological system can be accurately studied.

Caging of biomolecules is described by John Corrie in Dynamic Studies in Biology (2005, editors Goeldner and Givens, Wiley-VCH Verlag GmbH&Co. KGaA, Weinheim).

WO04085394A1 to Corrie et al. describes 7-nitroindoline compounds which include a triplet sensitizing group such as substituted or unsubstituted benzophenone group and can be used to cage neurotransmitter effector species.

U.S. Pat. Nos. 5,430,175 and 5,587,509 to Hess et al. describe caged carboxyl compounds and methods of releasing carboxyl compounds in which a 2-alkoxy-5-nitrophenyl photosensitive group blocks a carboxyl function. Preferred compounds are caged neuroactive amino acids (e.g., glutamate and GABA [gamma-aminobutyric acid]) with carboxynitrobenzyl chromophores (CNB) photolyzable by laser pulses at wavelengths above about 350 nm within about 3 microseconds and provide a product quantum yield of greater than about 0.2.

U.S. Pat. No. 5,034,613 to Denk et al. describes a two-photon excitation method that allows accurate spatial discrimination and permits quantification of fluorescence from small volumes whose locations are defined in three dimensions. The two-photon excitation method provides a depth of field resolution comparable to that produced in confocal laser scanning microscopes without the disadvantages of confocal microscopes, previously described. This is especially important in cases where thicker layers of cells are to be studied. Furthermore, the two-photon excitation greatly reduces the background fluorescence.

The photonic flux required for uncaging is typically even more demanding to cell viability than that of fluorescence microscopy. This is because the caging chromophore first deployed for a bio-molecule in 1977 (the ortho-nitrobenzyl photochemical protecting group, Engels & Schlaeger, 1977) and used in the vast majority of uncaging experiments since then, does make efficient use of the incident light. Thus, new caging chromophores that absorb and use light more efficiently so as to be less damaging to cells are desired to address shortcomings of known chromophores, especially for 2-photon excitation uncaging.

All references cited herein are incorporated herein by reference in their entireties.

BRIEF SUMMARY OF THE INVENTION

Inventors have discovered that nitrodibenzylfuran nitrocarbazole derivatives can be used to cage and photorelease an effector molecule, e.g., metals such as calcium, magnesium, aminoacids, such as, glycine, gamma amino butyric acid or glutamate, from a caged state by illumination.

The invention includes a photolabile compound comprising a chromophore having a structure based on a three ring fusion wherein two rings are benzyl rings one of which has a nitro group in a 3-position and wherein the two benzyl rings are fused with a heterocycle having 4 carbons and a heteroatom.

The invention includes photolabile compound wherein the chromophore is depicted by the formula

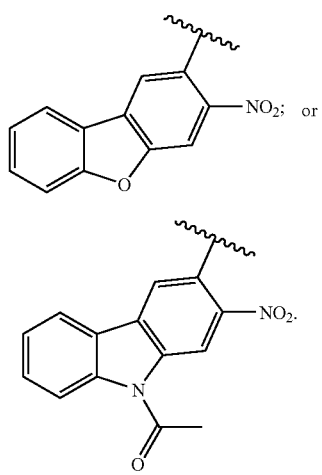

In certain embodiments of the present invention, the chromophore is depicted by the formula

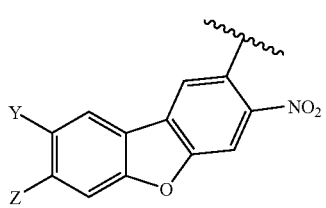

wherein Y=H, OMe, OEt, OPr, $O(CH_2)_n CO_2H$, $(CH_2)_n CO_2H$ and Z=H, OMe, OEt, OPr, $O(CH_2)_n CO_2H$, $(CH_2)_n CO_2H$; or

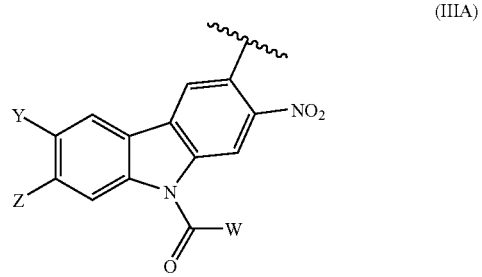

In certain embodiments of the present invention, the chromophore comprises a functional group suitable for covalent or ionic binding of an effector wherein the functional group is bound to the chromophore to form a functionalized chromophore.

The invention further includes a method of synthesizing nitrodibenzylfuran and derivatives and analogs thereof. The invention also includes various intermediates prepared in the synthesis.

Further, the invention includes a compound of the formula:

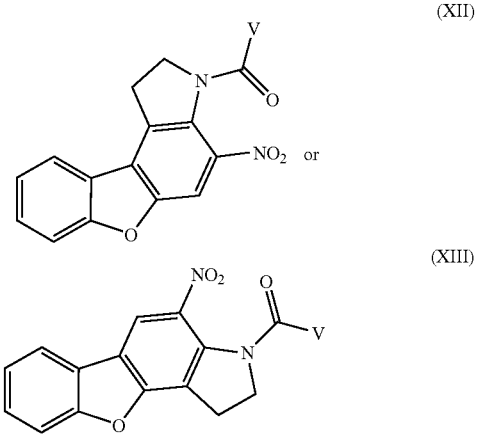

wherein V is an amino acid. A derivative can be made by substituting any hydrogen for OMe, OEt, OPr, $O(CH_2)_n CO_2H$, and $(CH_2)_n CO_2H$.

Further included is a method of photochemical release an effector molecule from a caged compound, the method comprising:
  (a) preparing a caged compound comprising a chromophore of claim 1; and
  (b) photolyzing the caged compound with light to release the effector molecule.

In certain embodiments, the caged compound comprises at least one structure depicted by at least one of the formulas (I)-(XXIX).

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The present invention is directed to new caging chromophore nitrodibenzylfuran (NDBF thereafter).

Figure 1A:
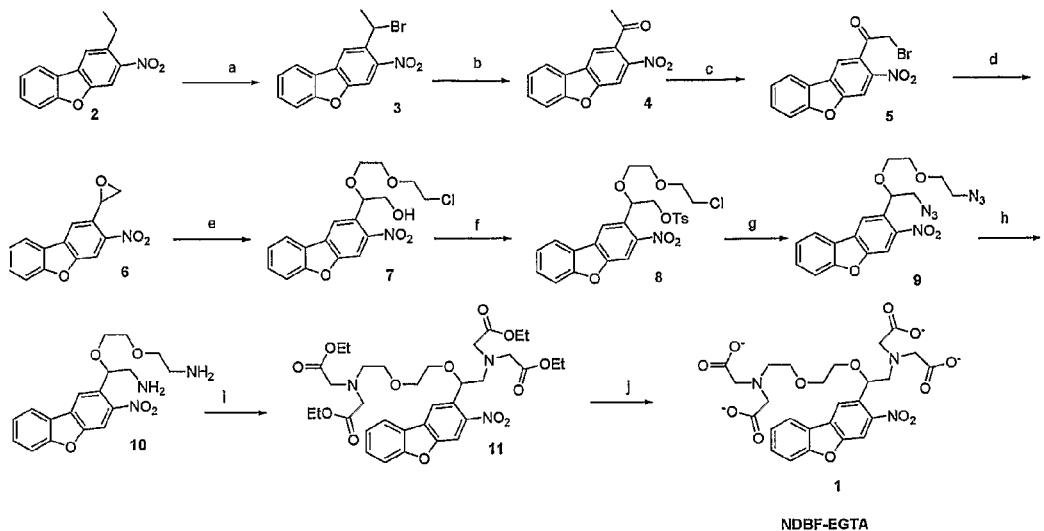
FIG. 1A is a scheme depicting synthesis of NDBF-EGTA.
Figure 1B:
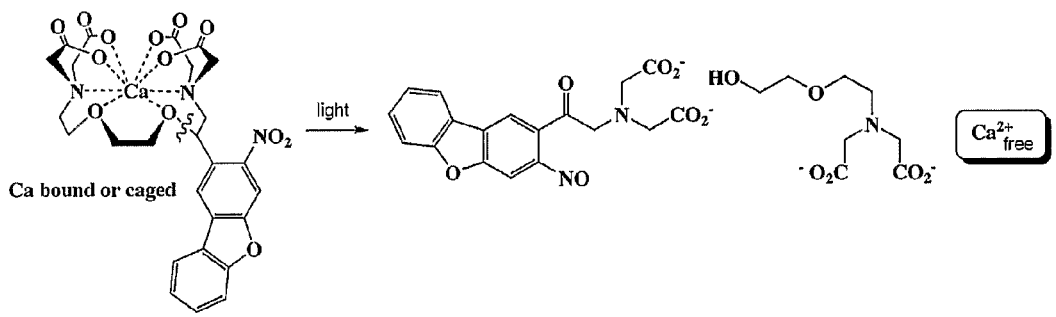
FIG. 1B is a scheme demonstrating photorelease of caged Ca cation.

Inventors have synthesized a new caging chromophore nitrodibenzylfuran (NDBF) as described in FIG. 1A that is about 50 times more efficient than known nitrobenzyl cages (see Table 1). In other embodiments, an improvement in 5-20 times was observed. One of the applications of this new chromophore is to a caged Ca. Another non-limiting example of the application of the new chromophore is to cage amino acids (see FIGS. 5 and 10).

The extinction coefficient ($\epsilon$) and the quantum yield ($\phi$) are the two photochemical properties that define the efficiency of a chromophore. The former is an absolute value of a chromophore; the latter depends upon the exact nature of the photolyzed bond, as well as the chromophore itself. The four most widely used caged compounds (ATP, IP3, glutamate, Ca) with the ortho-nitrobenzyl chromophore have $\epsilon$ and $\phi$ in the range of 430-970 and 0.14-0.63. The product ($\epsilon \cdot \phi$) for each caged compound defines the efficiency of use of the incident light. These data, along with rates of release, for the most widely used caged compounds (and commercially available) are summarized in Table 1 below.

TABLE 1

| Chromophore | Effector | $\epsilon/M^{-1}cm^{-1}$ | $\phi$ | Rate/s$^{-1}$ | $\epsilon \cdot \phi$ |
|---|---|---|---|---|---|
| nitrobenzyl | ATP | 430 | 0.63 | 83 | 271 |
| | IP3 | 430 | 0.65 | 230 | 150 |
| | glutamate | 500 | 0.14 | 50,000 | 70 |
| | Calcium | 970 | 0.20 | 68,000 | 194 |
| DMNB | ATP | | 0.07 | 18 | |
| | cAMP | | 0.05 | 300 | |
| | Ca/Mg | 4,300 | 0.18 | 38,000 | 774 |
| NDBF | Calcium | 18,400 | 0.6 | 25,000 | 11,000 |

NDBF has an $\epsilon$ of 18,400 and NDBF-EGTA has a $\phi$ of photolysis of about 0.6 and a 2-photon cross-section of 0.3-0.6 GM. Thus, NDBF-EGTA makes ultra-efficient use of incident light.

Photolabile Compounds of the Invention

Since it is well known that simple nitrobenzyl cages work for all functional groups (Corrie & Trentham 1993, Ellis-Davies 2005, Corrie 2005), inventors expect the caging chromophore of the invention to be similarly useful, and generically applicable for all functional groups.

Photolabile compounds of the invention comprise a chromophore which has a structure based on a three ring fusion wherein two rings are benzyl rings one of which has a nitro group in a 3 position and wherein the two benzyl rings are fused with a heterocycle having 4 carbons and a heteroatom (e.g., nitrogen, oxygen, etc). Preferred chromophores have the following formula:

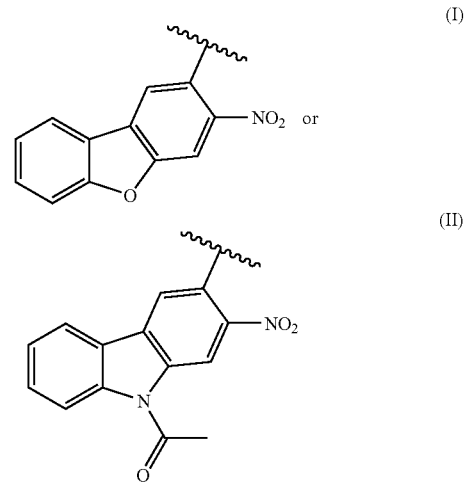

Derivatives of the chromophore of the invention can be made by substitutions of hydrogen in any position of a benzyl ring, for example, as depicted by the following formula

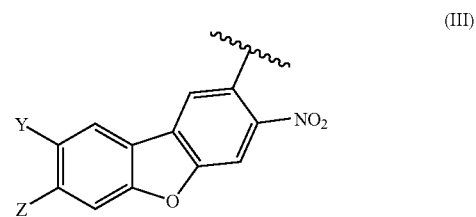

wherein Y=H, OMe, OEt, OPr, O(CH$_2$)$_n$CO$_2$H, (CH$_2$)$_n$CO$_2$H and Z=H, OMe, OEt, OPr, O(CH$_2$)$_n$CO$_2$H, (CH$_2$)$_n$CO$_2$H; or

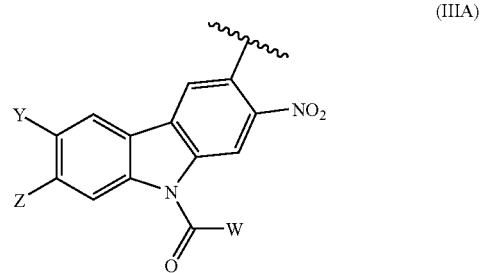

wherein W=H, Me, Et, Pr, CO$_2$H, (CH$_2$)$_n$CO$_2$H, CH$_2$, CHMe, CMe$_2$, (CH$_2$)$_n$PO$_3$H$_2$, (CH$_2$)$_n$SO$_3$H.

Functionalized Chromophore

The chromophore of the invention is then modified to contain a function group to form a functionalized chromophore. The functional group can be any chemical group suitable for either covalent or ionic binding of an effector to the chromophore to form a caged photolabile compound. Non-limiting examples of functionalized chromophores are depicted by the following formulas:

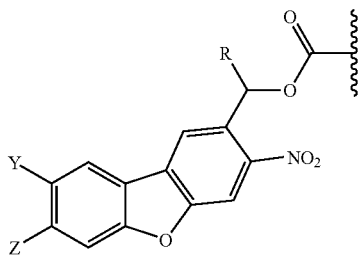

(IV)

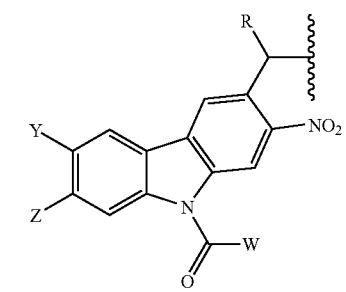

(V)

In a preferred embodiment of the invention, functionalized chromophores have a chelating group such as for example, a derivative of EGTA and EDTA. Preferred functionalized chromophores include NDBF-EGTA and NDBF-EDTA as depicted by formulas (VI) and (VII) below

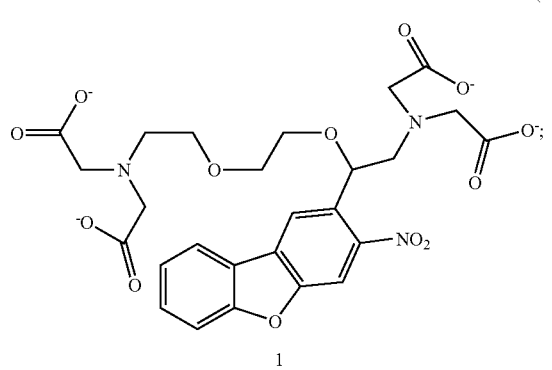

1
NDBF-EGTA (VI)

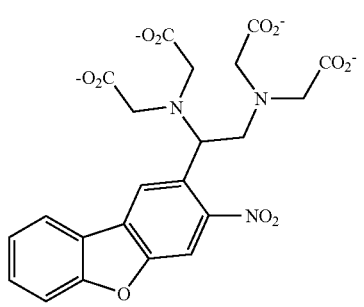

(VII)

Another preferred embodiment of functionalized chromophores includes the chromophore of the invention modified with functional groups suitable for binding a corresponding group of an amino acid. In one preferred embodiment, the functional group is an indolinyl group as depicted by formulas (VIII) and (IX) below:

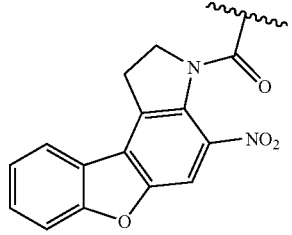

(VIII)

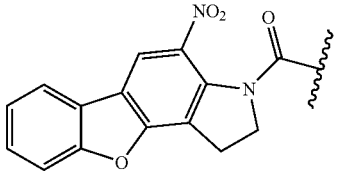

(IX)

In certain embodiments, the chromophore of the invention is functionalized to contain a halogen group, e.g., a bromine group. As functionalized caging chromophores, NDBF halides (e.g., NDBF bromides (compounds 3, 24, and 28) depicted by formulas (XX-XXII) and NDBF chloride (XXIII) can be used to react with the following types of functionalities: amines, thiols, phenols, acids, phosphates, thiophosphates, alcohols and carboxylates. They are especially useful for direct caging of the following biologically important compounds: thionucleotides (e.g., ATP-gamma-S); thioinositols and inositols; enzymes and peptides containing lysines, cystienes and thiophosphates; glutamate; GABA; anisomycin and non-amino acid neurotransmitters such as serotonin and dopamine.

In certain embodiments, the chromophore of the invention contains oxycarbonyl chloride as depicted by formula (XIX), Example 9. Oxycarbonyl chlorides have been used extensively to cage molecules as they are very reactive in very mild conditions, and can be used to react with the following types of functionalities: amines, thiols, phenols, and alcohols. They are especially useful for the direct caging of the 5' (five-prime) end of nucleosides as they react well with such alcohols. Thus they can also be used for caging inositols on the 6-hydroxy position, or caging antibodies, enzymes or peptides on reactive lysines by direct conjugation with the amine side chain of the lysine.

Caged Compounds

Next, the functionalized chromophore is reacted with an effector to cage the effector and thereby form a caged photolabile compound of the invention and thus shield a measurable activity of the effector. Examples of the measurable activity of the effector include activation of muscle contraction, neurotranmission, protein expression, ion channel opening, and cell motility.

The effector or a caged substrate X (see formulas (X)-(XI) and (XIA) may be any type of molecule that can be bound either covalently or ionically to the functionalized chromophore of the invention. One example of the effector is a bioactive molecule. Non-limiting examples of such biomolecules include amino acids, peptides, proteins, calcium mobilizing agents (IP2, IP3, IP4, IP5, IP6, PIP2, cyclic-ADPribose, sphingosine-1-phosphate, sphingosine, NAADP, diacylglycerol), neurotransmitters, arachidonic acid, sugars, nucleotides and nucleosides, adrenergic agonists. Also fluorophores, biotins, crosslinkers and calcium chelators maybe caged using the same photochemical protecting groups.

The caged substrate, the effector, may also be any organic molecule used in organic synthesis. Manipulation of protecting groups during a synthetic sequence is one of the central problems of organic chemistry. Most protecting groups are cleaved using thermal chemistry. Thus, photochemical protecting groups are orthogonal to almost all such thermal chemistry, making them extremely useful, as they may be used in parallel to traditional thermal chemistry.

Figure 5:
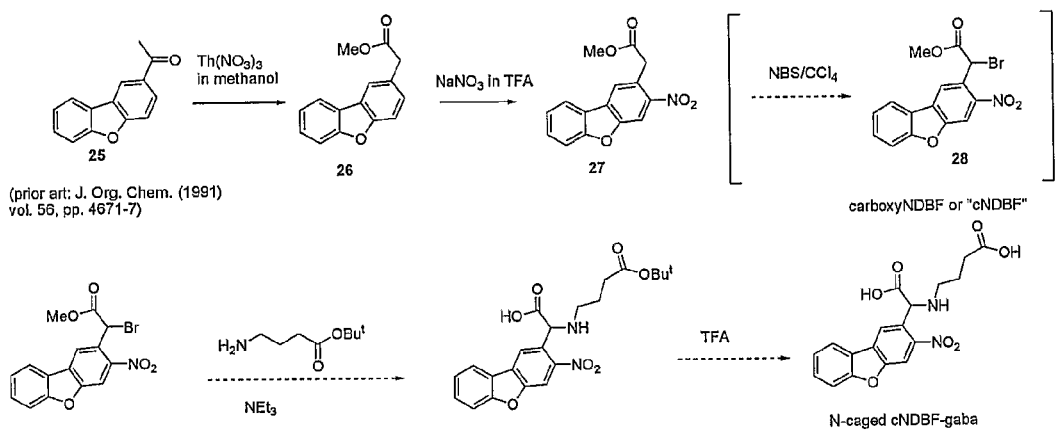
FIG. 5 is a scheme demonstrating synthesis of cNDBF caging group and cNDNF-caged GABA.
Figure 10:
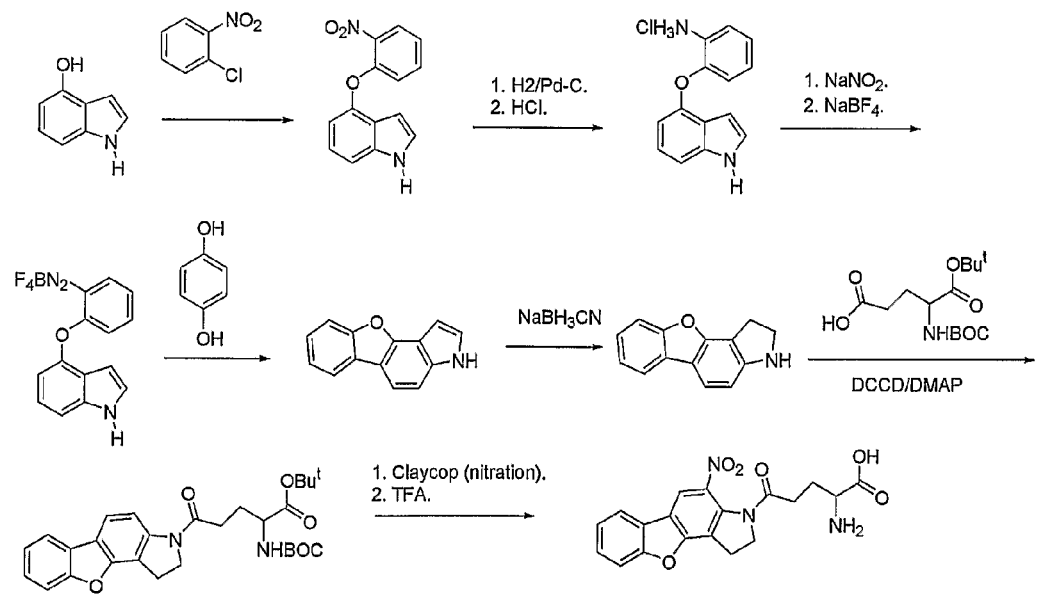
FIG. 10 is a scheme demonstrating synthesis of caged glutamate.

Examples of synthesis of caged photolabile compounds of the invention are shown in FIGS. 5 and 10.

In certain embodiments, the caged photolabile compound of the invention is depicted by the following formulas:

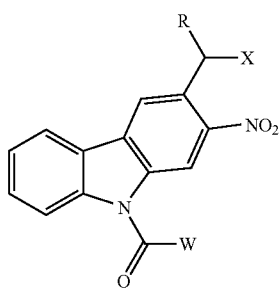

(X)

wherein W=H, Me, Et, Pr, $CO_2H$, $(CH_2)_nCO_2H$, $CH_2$, CHMe, COHMe, $CMe_2$, $COMe_2$, $(CH_2)_nPO_3H_2$, $(CH_2)_n SO_3H$; R=H, Me, Et, Pr, $CO_2H$, $(CH_2)_nCO_2H$, $CH_2$, CHMe, COHMe, $CMe_2$, $COMe_2$, $(CH_2)_nPO_3H_2$, $(CH_2)_n SO_3H$; and n is an integral if 0 to 10.

In certain embodiments, the caged photolabile compound of the invention is depicted by the following formulas:

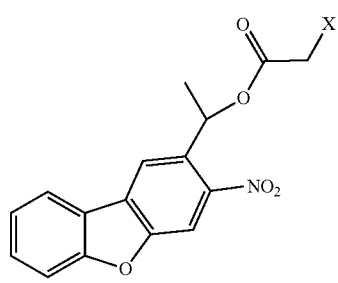

(XI)

In certain embodiments, derivatives of the caged photolabile compound of the invention is depicted by the following formula:

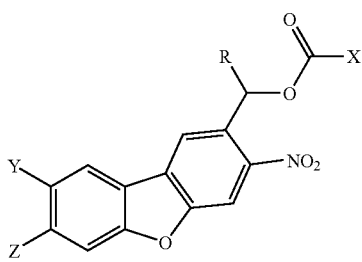

(XIA)

R=H, Me, Et, Pr, $CO_2H$, $(CH_2)_nCO_2H$, $COH_2$, COHMe, $COMe_2$, $(CH_2)_nPO_3H_2$, $(CH_2)_nSO_3H_2$.
Y=H, OMe, OEt, OPr, O(CH2)$_n$CO2H, (CH2)$_n$CO2H
Z=H, OMe, OEt, OPr, O(CH2)$_n$CO2H, (CH2)$_n$CO2H
X=caged substrate In certain embodiments, the caged photolabile compound of the invention is depicted by the following formula:

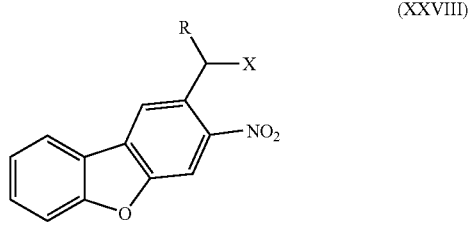

(XXVIII)

R=H, Me, Et, Pr, OMe, OEt, OPr, $O(CH_2)_nCO_2H$, $(CH_2)_n CO_2H$; $(CH_2)_nSO_2H$; $(CH_2)_nPO_3H_2$

In certain embodiments, derivatives of the caged photolabile compound (XXVIII) of the invention is depicted by the following formula:

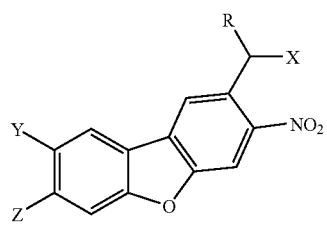

(XXIX)

In certain embodiments, the caged photolabile compound of the invention is a caged amino acid wherein the functionalized chromophore of the invention is used to cage amino acids through an indolinyl linkage (see formulas XII-XIII below, wherein V is an amino acid):

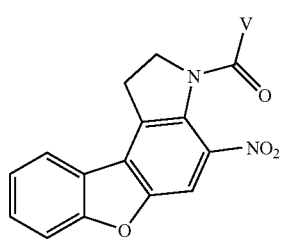

(XII)

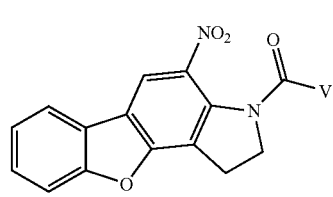

(XIII)

As described above, derivatives can be made by substituting at least one hydrogen in the chromophore structure by OMe, OEt, OPr, $O(CH_2)_nCO_2H$, and $(CH_2)_nCO_2H$.

Preferred caged amino acids are tyrosine, glutamate and GABA as depicted by formulas below

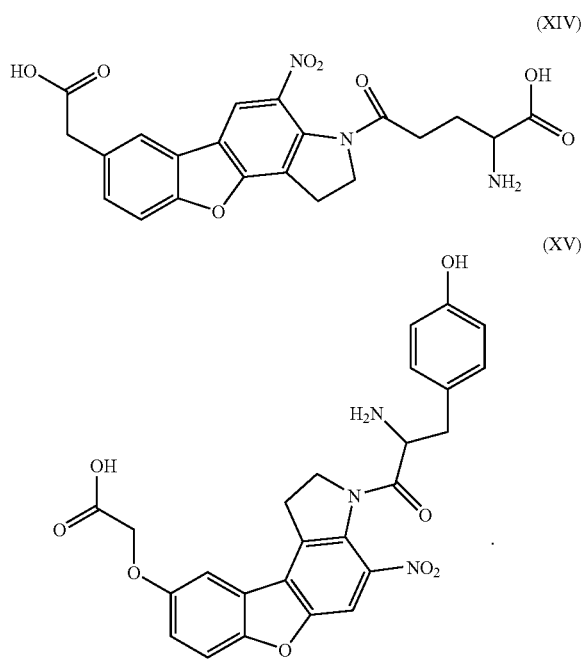

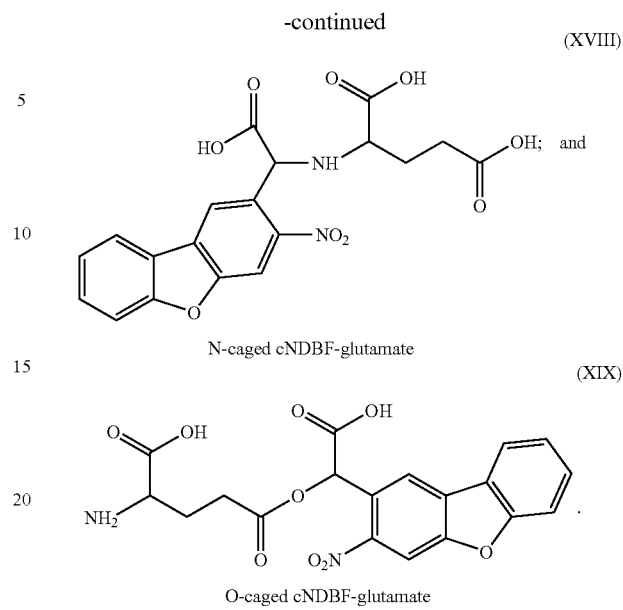

Caged neurotransmitters (cNDBF) can be obtained by combining the functionalized chromophore of the invention with desired aminoacids using methods described in U.S. Pat. Nos. 5,430,175 and 5,587,509 to Hess et al. as shown in FIG. 5.

The functionally reactive cNDBF bromide may be coupled directly either to the N- or C-terminus to the requisitely protected amino acids (glutamate and gamma-aminobutyric acid) to yield caged neurotransmitters (XVI)-(XIX).

Examples of caged neurotransmitters of the invention are depicted by the following formulas:

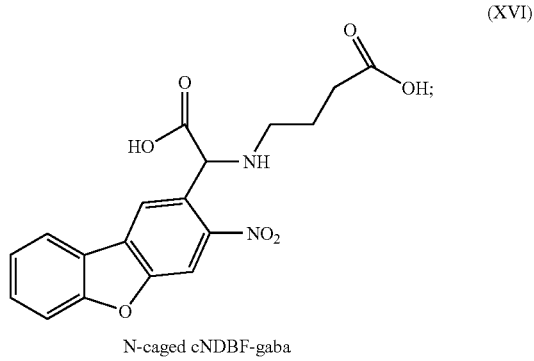

In certain embodiments, the caged photolabile compound of the invention is a nucleobase, as depicted by formula (XXIV)

General structure of NDBFoxcarbonyl-caged nucleotides (R═OH; base═adenine, guanine, thymine, cytosine) and their de-oxynucleotides equivalents (i.e., R═H) for building DNA and RNA fragments using standard solid-phase synthetic organic chemistry for the construction of DNA and RNA fragments.

Synthesis of the photolabile compound of the invention will now be described using NDBF-EGTA as an example.

The photolabile Ca-specific chelator (NDBF-EGTA) was synthesized in 10 steps. The synthesis of NBDF-EGTA 1 is outlined in FIG. 1A. It starts with the known 3-nitro-2-ethyldibenzofuran, 2.

Compound 2 can be made as described by Pharmaceutical Bulletin (1957) vol 5 pp. 539-543. However, it was not appreciated prior to this invention that NDBF can be used as a caging chromophore. Further, inventors have discovered that NDBF can be used as a chromophore that is highly sensitive to uncaging, especially in 2-photon excitation mode, and thus use of NDBF as a generic caging chromophore provides results far more superior to the previously used nitrobenzyl and dimethoxynitrobenzyl generic caging chromophores (i.e., NDBF has 2-photon cross section of at least 0.3 GM, and efficiency of use of near-UV uncaging light of above 10,000).

1-Bromo-1-(3-nitrodibenzofuran-2-yl)-ethane (compound 3)

A mixture of compound 2 (6.45 g, 26.8 mmol), NBS (4.81 g, 27.0 mmol) and benzoylperoxide (121 mg, 0.5 mmol) in CCl$_4$ (250 ml) was refluxed for 4 h. After cooling down to RT, mixture was diluted with CH$_2$Cl$_2$, washed with 1% NaHCO$_3$, dried over MgSO$_4$, and evaporated. Flash chromatography [hexanes/CH$_2$Cl$_2$ (1:2)] gave 2 as white solid (7.02 g, 82%); mp 119-121 C (decomposed); IR: $v_{max}$/cm$^{-1}$ 1535, 1355; $^1$H NMR: δ (300 MHz, CDCl$_3$) 8.39 (s, 1H), 8.05 (s, 1H), 8.03 (d, J=6.8 Hz, 1H), 7.63-7.23 (m, 3H), 5.98 (dd, J=6.8 Hz, 1H), 2.20 (d, J=6.8 Hz 3H); $^{13}$C NMR δ (75 MHz, CDCl$_3$) 158.5, 154.3, 133.3, 130.0, 129.9, 129.2, 124.1, 122.5, 122.0, 121.7, 112.5, 108.7, 43.0, 28.2.

1-(3-Nitrodibenzofuran-2-yl)-ethanone (compound 4)

A mixture of NaHCO$_3$ (1.01 g, 12 mmol) and compound 3 (3.56 g, 11.2 mmol) in DMSO (100 ml) was stirred at 70 C for 2 h. The solution was poured into ice-cold water and precipitated pale brown solid was filtered, washed with water and dried in vacuo gave almost pure compound 3 (2.36 g, 83%). mp 184-186 C; IR: $v_{max}$/cm$^{-1}$ 1700, 1530, 1420, 1330; $^1$H NMR: δ (300 MHz, CDCl$_3$) 8.30 (s, 1H), 8.03 (d, J=7.9 Hz, 1H), 7.99 (s, 1H), 7.70-7.60 (m, 2H), 7.47 (t, J=7.9 Hz, 1H), 2.63 (s, 3H); $^{13}$C NMR δ (75 MHz, CDCl$_3$) 199.6, 158.7, 155.3, 133.8, 130.3, 129.6, 124.5, 122.3, 122.1, 121.8, 119.6, 112.7, 108.9, 30.8.

2-Bromo-1-(3-nitrodibenzofuran-2-yl)-ethanone (compound 5)

A solution of 4 (2.36 g, 9.24 mmol) in AcOH—CH$_2$Cl$_2$ (1:2, 200 ml) was added Br$_2$ (0.48 ml, 9.30 mmol) and was stirred at RT for 8 h. The solution was evaporated to give 5 (3.04 g, 99%). mp 217-218° C. (decomposed); IR: $v_{max}$/cm$^{-1}$ 1720, 1530, 1425, 1345; $^1$H NMR: δ (300 MHz, CDCl$_3$) 8.43 (s, 1H), 8.06 (d, J=7.7 Hz, 1H), 8.04 (s, 1H), 7.72-7.63 (m, 2H), 7.49 (t, J=7.7 Hz, 1H), 4.36 (s, 2H).

2-(3-Nitrodibenzofuran-2-yl)-oxirane (compound 6)

To a solution of 5 (3.03 g, 9.10 mmol) in dioxane-MeOH (3:1, 100 ml) was added NaBH$_4$ (9.1 mmol, 345 mg) at 4oC, and was stirred for 30 min at the same temperature. The mixture was treated with NaOH. (70 ml, 2.5 N) and stirred for 30 min at RT and evaporated. Residue was diluted with CH$_2$Cl$_2$ (100 ml), washed with water, brine solution, dried over MgSO$_4$ and evaporated. Column chromatography [hexane/AcOEt (10:1)] gave white solid 6 (1.67 g, 72%). mp 150-152 C (decomposed); IR: $v_{max}$/cm$^{-1}$ 1535, 1435, 1350; $^1$H NMR: δ (300 MHz, CDCl$_3$) 8.42 (s, 1H), 8.19 (s, 1H), 8.03 (d J=7.7 Hz, 1H), 7.66-7.57 (m, 2H), 7.44 (t, J=8.0 Hz), 4.61 (dd, J=4.4 and 2.6 Hz, 1H), 3.37 (dd, J=5.5 and 4.4 Hz, 1H), 2.74 (dd, J=5.5 and 2.6 Hz, 1H).

2-[2-(2-Chloroethoxy)-ethoxy]-2-(3-nitrodibenzofuran-2-yl)-ethanol (compound 7)

To a mixture of 2-(2-chloroethoxy)-ethanol (65 mmol, 8.13 g) and TsOH (30 mg), solution of 6 (6.54 mmol, 1.67 g) in CH$_2$Cl$_2$ (10 ml) was added at RT then stirred at 90 C for 2 h. After cooling down to RT, the mixture was diluted with CH$_2$Cl$_2$, washed with 5% NaHCO$_3$, dried over MgSO$_4$ and evaporated. Column chromatography [Hexans-AcOEt (3:2)] gave pale orange solid 7 (544 mg, 22%). mp 56-57 C; IR: $v_{max}$/cm$^{-1}$ 1530, 1430, 1340; $^1$H NMR: δ (300 MHz, CDCl$_3$) 8.37 (s, 1H), 8.24 (s, 1H), 8.06 (d, J=7.7 Hz, 1H), 7.65-7.57 (m, 2H), 7.44 (t, J=8.0 Hz), 5.26 (dd, J=7.3 and 3.1 Hz, 1H), 4.01 (dd, J=11.7 and 3.3 Hz, 1H), 3.79-3.62 (m, 9H).

2-[1-[2-(2-Chloroethoxy)-ethoxy]-2-(p-toluenesulphonyl)-ethyl]-3-nitrodibenzofuran (compound 8)

A mixture of 7 (542 mg, 1.43 mmol) and Ts$_2$O (1.95 g, 6.0 mmol) in dry pyridine (30 ml) was stirred at RT for 0.5 h. After evaporation of pyridine, AcOEt was added to the residue and washed with 1N HCl, saturated NaHCO$_3$ solution and brine. The mixture was dried and evaporated. Column chromatography [Hexane-AcOEt (2:1)] gave compound 8 as an orange oil (534 mg, 70%). IR: $v_{max}$/cm$^{-1}$ 1530, 1430; $^1$H NMR: δ (300 MHz, CDCl$_3$) 8.33 (s, 1H), 8.19 (s, 1H), 8.04 (d, J=7.9 Hz, 1H), 7.69-7.59 (m, 4H), 7.46 (t, J=6.8 Hz), 7.18 (d, J=8.1 Hz, 2H), 5.39 (dd, J=6.2 and 3.2 Hz, 1H), 4.41 (dd, J=10.6 and 3.2 Hz, 1H), 4.34 (dd, J=10.6 and 6.2 Hz, 1H), 3.73-3.53 (m, 8H), 2.35 (s, 3H).

2-[2-azido-1-[2-(2-azidoethoxy)-ethoxy]-ethyl]-3-nitrodibenzofuran (compound 9)

A solution of 8 (534 mg, 1.0 mmol), sodium iodide (600 mg, 4.0 mmol) and sodium azide (260 mg, 4.0 mmol) in DMF (5 ml) was stirred at 90 C for 3 h. After evaporation of DMF, CH$_2$Cl$_2$ was added to the residue, washed with water, dried over MgSO$_4$ and evaporated. Column chromatography [Hexanes-AcOEt (5:1)] gave white powder 9 (377 mg, 92%). mp 112-113° C.; IR: $v_{max}$/cm$^{-1}$ 2140, 1530, 1435; $^1$H NMR: δ (300 MHz, CDCl$_3$) 8.43 (s, 1H), 8.28 (s, 1H), 8.09 (d J=7.7 Hz, 1H), 7.67-7.58 (m, 2H), 7.49-7.44) (m, 1H), 5.38 (dd, J=6.8 and 3.5 Hz, 1H), 3.79-3.51 (m, 8H), 3.43-3.38 (m, 2H).

2-[2-amino-1-[2-(2-aminoethoxy)-ethoxy]-ethyl]-3-nitrodibenzofuran (compound 10)

A solution of 9 (230 mg, 0.56 mmol) and Ph$_3$P (880 mg, 3.35 mmol) in dioxane (10 ml) was refluxed for 1 h. 2.5N NaOH (2 ml) and EtOH (2 ml) were added to the reaction solution and stirred at 90 C for 1.5 h. After evaporation of dioxane, the residue was diluted with CH$_2$Cl$_2$, washed with 5N NaOH, dried over MgSO$_4$ and evaporated. Column chromatography [CH$_2$Cl$_2$-MeOH-Et$_3$N (70:30:3)] gave 10 (172 mg, 85%). mp 88-90° C.; IR: $v_{max}$/cm$^{-1}$ 1535, 1435; $^1$H NMR: δ (300 MHz, CDCl$_3$) 8.36 (s, 1H), 8.24 (s, 1H), 8.06 (d, J=7.9 Hz, 1H), 7.66-7.57 (m, 2H), 7.47-7.42 (m, 1H), 5.15 (dd, J=8.0 and 3.0 Hz, 1H), 3.71-3.53 (m, 6H), 3.21 (dd, J=13.5 and 3.0 Hz, 1H), 3.00-2.93 (m, 3H).

{2-[2-[2-(bis-ethoxycarbonylmethylamino)-ethoxy]-ethoxy]-2-(3-nitrodibenzofuran-2-yl)-ethyl]-ethoxycarbonylamino}acetic acid ethylester (compound 11)

To a solution of 10 (172 mg, 0.48 mmol), diisopropyl ethylamine (309 mg, 2.4 mmol) and sodium iodide (720 mg, 4.8 mmol) in dry CH$_3$CN (6.0 ml), ethyl bromoacetate (801 mg, 4.8 mmol) were added slowly and refluxed for 12 h. The mixture was evaporated, diluted with CH$_2$Cl$_2$ and filtered salts off. The filtrate was evaporated. Column chromatography [Hexanes-AcOEt (1:3)] gave pale orange oil 11 (240 mg, 71%). IR: $v_{max}$/cm$^{-1}$ 1700, 1530, 1430, 1340; $^1$H NMR: δ (300 MHz, CDCl$_3$) 8.38 (s, 1H), 8.21 (s, 1H), 8.09 (d. J=7.9 Hz, 1H), 7.65-7.56 (m, 2H), 7.47-7.42 (m, 1H), 5.31 (dd, J=6.1 and 4.0 Hz, 1H), 4.20-4.07 (m, 8H), 3.79 (s, 2H), 3.78 (s, 2H), 3.63-3.46 (m, 10H), 3.15 (ddd, J=6.2, 4.0, and 2.4 Hz, 2H), 3.00-2.90 (m, 2H), 1.33-1.19 (m, 12H); $^{13}$C NMR δ (75 MHz, CDCl$_3$) 171.9 (4C=O), 158.5, 154.2, 147.0, 132.1, 129.6, 124.0, 122.8, 122.3, 120.7, 112.4, 110.0, 108.7, 78.5, 70.6, 70.4, 69.2, 62.0, 60.8 (2CH$_2$), 60.7 (2CH$_2$), 56.1

(4CH$_2$), 54.1, 14.7 (2CH$_3$), 14.6 (2CH$_3$); FAB-MS: m/z (M+H)$^+$ Calcd for C$_{34}$H$_{45}$N$_3$O$_{13}$+Na: 726.2850. Found 726.2848.

NDBF-EGTA (compound 1)

A solution of 11 (82 mg, 0.116 mmol) and KOH (34 mg, 0.612 mmol) in MeOH (3 ml) was stirred at 60 C for 1 h. The solution was evaporated and dried in vacuo to give 1 quantitatively as a potassium salt. $^1$H NMR: δ (300 MHz, D$_2$O) 8.40 (s, 1H), 8.26 (s, 1H), 8.13 (d, J=7.9 Hz, 1H), 7.69-7.62 (m, 2H), 7.51-7.46 (m, 1H), 5.35 (dd, J=8.4 and 2.4 Hz, 1H), 3.70-3.63 (m, 2H), 3.57-3.38 (m, 8H), 3.13-2.99 (m, 6H), 2.76-2.67 (m, 1H), 2.64-2.55 (m, 1H); FAB-MS: m/z (M+H)$^+$ Calcd for C$_{26}$H$_{25}$N$_3$O$_{13}$K$_5$+K: 781.9572. Found 781.9577.

Ca Affinity of NDBF-EGTA

The high affinity, Ca-specific chelator EGTA is the basis of the new Ca cage. An EDTA derivative can be used for caging Mg. Thus, it is expected to have a high affinity for Ca in the physiological pH range (7.2-7.4). Inventors found that at pH 7.2 NDBF-EGTA has an apparent affinity for Ca of about 100 nM (cf. EGTA, 150 nM). At pH 7.5 there is a dramatic increase in Ca affinity, to 14 nM, and at pH 7.8 the values increases further to 5 nM. Inventors found that photolysis of the NDBF-EGTA:Ca complex in the presence of varying concentrations of Mg (from 0 to 10 mM), made no detectable difference to the amount of Ca uncaged, implying that NDBF-EGTA has a very low affinity for Mg of 15 mM at pH 7.2.

Quantum Yield of Photolysis

Inventors measured the quantum yield of photolysis of NDBF-EGTA by comparison with a known standard, 4-methoxy-7-nitroindolinyl(MNI)-glutamate (Matsuzaki, et al., 1999). A solution containing NDBF-EGTA and MNI-glutamate was photolyzed at 350 nm, in order to determine the relative % photolysis of the two caged compounds. The concentrations of the two compounds were set so that their chromophores would absorb the same amount of light (MNI/NDBF ratio 3.7:1), and so that the total optical density was 0.4. Under these conditions the same number of excited states are created simultaneously for both cages, making determination of the quantum for NBDF-EGTA more reliable. As a control, both cages were photolyzed separately to check that there was no interference from simultaneous photolysis. Inosine was also included in the photolysis reaction mixture, as a photochemically inert standard. MNI-glutamate has a quantum yield of photolysis of 0.085. Analysis of the reaction mixture by HPLC showed that NDBF-EGTA was photolyzed about 6-7 times faster than MNI-glutamate, implying a quantum yield of photolysis of 0.6. Saturating [Ca] had no effect on this value.

Two-Photon Photolysis.

Two-photon photolysis (2PP) of a solution contains MNI-glutamate (1.4 mM) and NDBF-EGTA (0.1 mM), by raster scanning the solution (256 pulses, 4 ms each, 300 mW). HPLC analysis of the reaction mixture showed that NDBF-EGTA was photolyzed 3-7 faster than MNI-glutamate, indicating the new caging chromophore has a 2-photon cross-section of 0.3-0.6 GM. Inventors have previously determined the 2P cross section of MNI-glutamate to be 0.06 GM.

Using the guidance provided in this disclosure and well known techniques, a skilled in the art will be able to make caged compounds of the invention.

Figure 3:
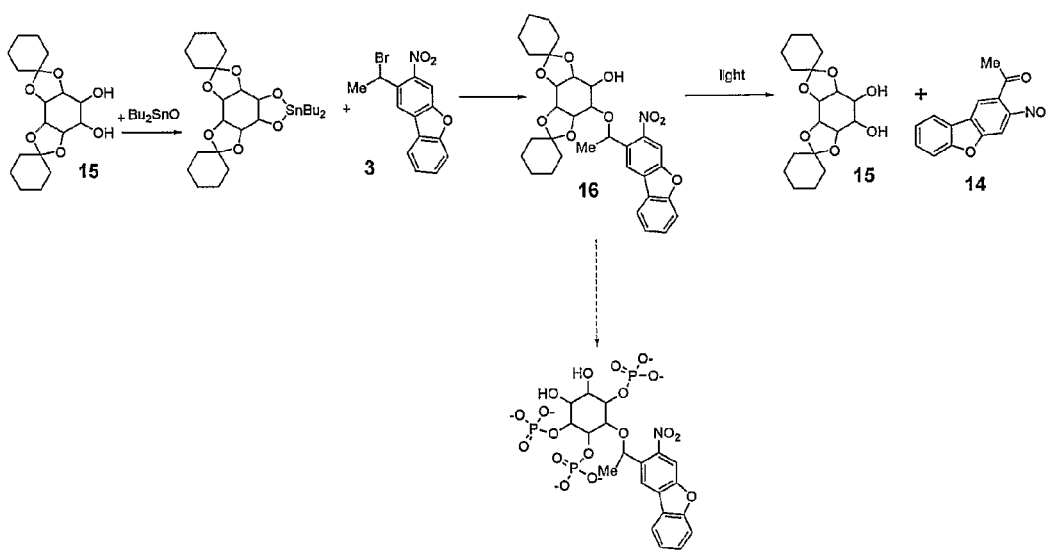
FIG. 3 is a scheme demonstrating synthesis and photochemistry of 6-NDBF-inositol derivative, wherein the dotted line depicts a prophetic example. Irradiation of 16 with near-UV light produces 15 and the same DBF nitrosoketone as in FIG. 2 as shown by NMR. Kantevari, et al., (2006) described making of 6-dimethoxynitrobenzyl-IP$_3$.
Figure 8:
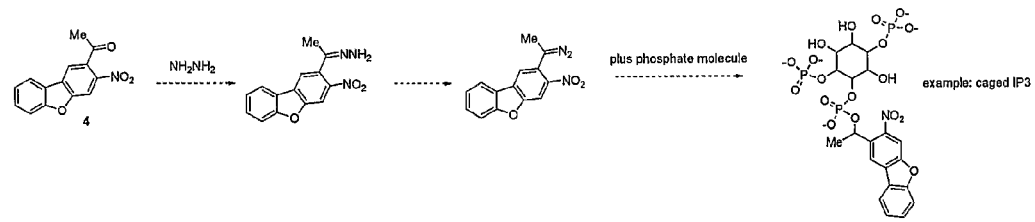
FIG. 8 is a scheme demonstrating synthesis of caged phosphates by azoNDBF coupling.

In certain embodiments of the invention, photolabile compounds are made as shown in FIGS. 3 and 8 and have the following formulas

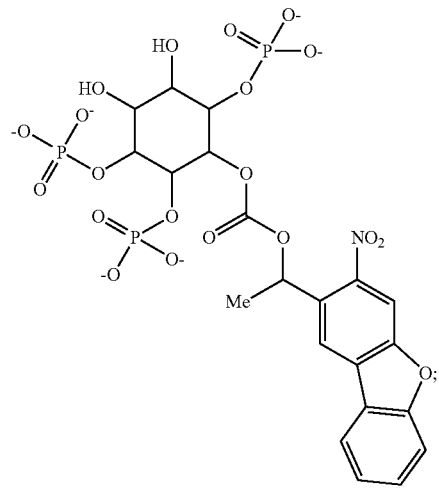

6-NBDF-IP3 (XXV)

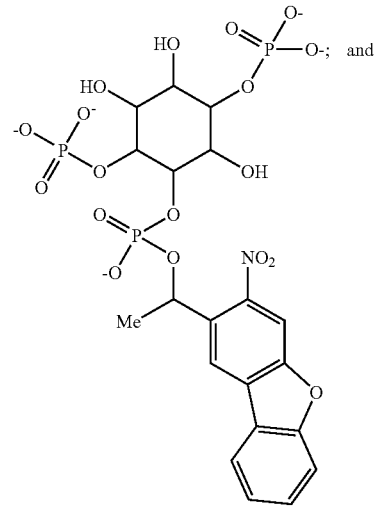

5-NDBF-IP3 (XXVI)

and

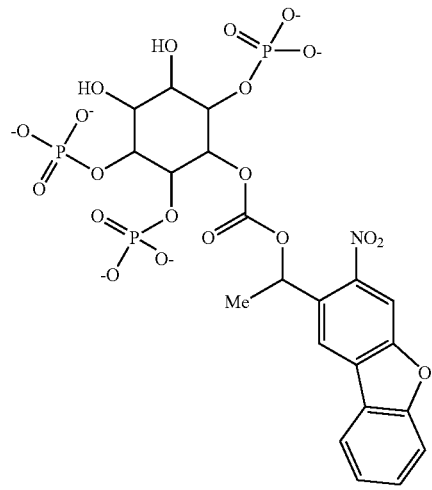

6-NBDFoxcarbonyl-IP3 (XXVII)

6-NDBFoc-IP3 can be made by coupling compound of formula (XXIII) to IP3.

Photolysis of Caged Compounds

After administration, the photolabile compound can be activated to release the effector species, by exposure to light, e.g., for by exposure to a flash of near-UV light, or two-photon excitation as described by U.S. Pat. No. 5,034,613 to Denk et al.

The light source for photolysis depends on the preparation and type of study, and should be chosen so that it gives uniform release of the caged compound throughout the preparation (caged compounds are photolyzed in the 300-380 nm near-UV range). If insufficient energy is delivered, and non-uniform uncaging occurs, then much of the usefulness of the technique is lost. Frequency-doubled ruby lasers are most often used for contractile studies (Goldman, 1986, Rapp, et al., 1989). Flash lamps are adequate for secretory studies, and are normally coupled to a microscope via the epifluorescent port, producing uncaging in small areas, if a pin hole is used. In some cases illumination is effected from above the specimen plane, by reflection off a dichroic mirror, giving long-term concentration jumps of $Ca^{2+}$, as the cell and patch pipette are illuminated by this route (Thomas, et al., 1993). Continuous light sources are an alternative to pulsed ones. A shutter must be placed in the light path. Systems with Xe arc lamps and CW Ar lasers have been described in detail (Parker, 1992; Wang and Augustine, 1995). The development of solid state mode-locked Ti:sapphire lasers for 2-photon imaging techniques has raised the possibility of using the same light sources for uncaging. The idea of focal release from a caged compound was advanced by Denk in 1994 but has be only recently realized (Matsuzaki, et al. 2001).

All the flash-photolysis studies use pulsed lasers as the light source. These lasers produce rapid pulses of intense, monochromatic light (e.g. the frequency doubled ruby laser has a pulse-width of 35 ns and the Nd-YAG 3 ns). Flash lamps, on the other hand, have much longer pulses of about 1 ms. There are a number of practical advantages to the latter's low intensity per unit time (1) greater chemical conversion-if cage lysis takes much longer than non-photochemical de-excitation of the chromophore (e.g. 10 microseconds vs. 1 nanoseconds), then the chromophore may be re-excited many more times during the long light pulse from a flash lamp, thus giving a better chemical yield for the same unit of energy; (2) less artifacts produced by the light pulse itself; and (3) cost: a Nd-YAG laser costs about five times more than a flash lamp. One can make a N2 laser very cheaply though, Engert, et al., (1996)).

Two-Photon Excitation

Two-photon excitation is made possible, for example, as described in U.S. Pat. No. 5,034,613 to Denk et al., by the combination of (a) the very high, local, instantaneous intensity provided by the tight focusing available in a laser scanning microscope, wherein the laser can be focused to diffraction-limited waist of less than 1 micron in diameter, and (b) the temporal concentration of a pulsed laser. A high intensity, long wavelength, monochromatic light source which is focusable to the diffraction limit such as a colliding-pulse, mode-locked dye laser, produces a stream of pulses, with each pulse having a duration of about 100 femtoseconds ($100 \times 10^{-15}$ seconds) at a repetition rate of about 80 MHz. These subpicosecond pulses are supplied to the microscope, for example by way of a dichroic mirror, and are directed through the microscope optics to a specimen, or target material, located at the object plane of the microscope. Because of the high instantaneous power provided by the very short duration intense pulses focused to the diffraction limit, there is an appreciable probability that a fluorophore (a fluorescent dye), contained in the target material, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the microscope optics to a suitable detector.

The two-photon excitation of fluorophores by highly intense, short pulses of light constitutes a general fluorescence technique for microscopy which provides improved background discrimination, reduces photobleaching of the fluorophores, and minimizes the photo damage to living cell specimens. This is because the focused illumination produced in the microscope fills a converging cone as it passes into the specimen. All of the light that reaches the plane of focus at the apex of the converging cone, except the tiny fraction that is absorbed in the fluorophore, then passes out the opposite side of the specimen through a diverging cone. Only in the region of the focal point on the object plane at the waist formed by the converging and diverging cones is the intensity sufficiently high to produce two photon absorption in the specimen fluorophore, and this intensity dependence enables long wavelength light to provide the effect of short wavelength excitation only in the small local volume of the specimen surrounding the focal point. This absorption is produced by means of a stream of fast, high intensity, femtosecond pulses of relatively long wavelength that retains a moderate average illumination intensity of long wavelength light throughout the remainder of the specimen outside the region of the focal point. As a result, photobleaching of the fluorophore outside the plane of focus is virtually eliminated. One-photon absorption of the long wavelength light is negligible, and outside the plane of focus the instantaneous intensity is too low for appreciable two-photon absorption and excitation, even though the time average illumination is in reality nearly uniform throughout the depth of the specimen. This effect also significantly reduces the damage to living cells.

The two-photon excitation as described in U.S. Pat. No. 5,034,613 to Denk et al., allows accurate spatial discrimination and permits quantification of fluorescence from small volumes whose locations are defined in three dimensions, and thus provides a depth of field resolution comparable to that produced in confocal laser scanning microscopes without the disadvantages of confocal microscopes previously described. This is especially important in cases where thicker layers of cells are to be studied. Furthermore, the two-photon excitation greatly reduces the background fluorescence.

Uses for the Invention

This invention is useful for variety of biological and medicinal applications involving, for example, monitoring and affecting changes in signaling. As the caged compounds of the present invention are compatible with the biological conditions used in such cell based assays and are capable of releasing effecter species on irradiation, they are particularly suited in cell-based assays such as patch clamp experiments and high throughput screening methods. Patch clamp experiments are a widely used technique in biology that was originally developed to observe ionic current produced when ions flow through ion channels, membrane proteins that regulate the flow of ions across cellular membranes and hence the physiology of cells. This ionic movement creates an electrical current which is tightly regulated by specific signals that cause the ion channels to open and close. The movement of the ions leads to a measurable electrical current that forms the basis of processes such neuronal and neuromuscular communication.

This technique has found many applications including the observation of the function of proteins in lipid bilayers, monitoring the synaptic transmission between neurons in the brain and monitoring changes that occur in cell membranes during secretion. In basic terms, patch clamp experiments employ a pipette or capillary having an opening between about 0.1 and 5 microns. A portion of the cell wall of a single cell is sucked into the opening allowing potentials to be applied to and measured across the cell membrane. Patch clamping has been used in assays for the effect of drugs on cells particularly those used to affect ion channels such as sodium or potassium channels.

Thus, the compounds of the invention can be introduced into the vicinity of a cell, e.g., in a patch clamp experiment, and a concentration of the active effector species generated in very short period on irradiation. This enables the effect of the released species to be studies under controlled circumstances.

Several reports indicate progress towards high throughput screening in association with patch clamping, and neuroactive amino acids and their interactions with specific receptors are targets for therapeutic intervention. The ability to apply a sub-millisecond pulse of neuroactive amino acid to patch clamped cells within a multiple assay format is likely to be an important component of successful assays, avoiding the well-known desensitization of receptors on neuronal cells that occurs in the prolonged presence of the neuroactive amino acid. In one embodiment of such an assay, the array of patch clamped cells would be set up with specific test compounds together with the caged native neuroactive amino acid (such as L-glutamate, GABA or glycine) and the native compound would then be photoreleased by brief illumination of the array.

The invention will be illustrated in more detail with reference to the following Examples, but it should be understood that the present invention is not deemed to be limited thereto.

EXAMPLES

Example 1

Figure 2:
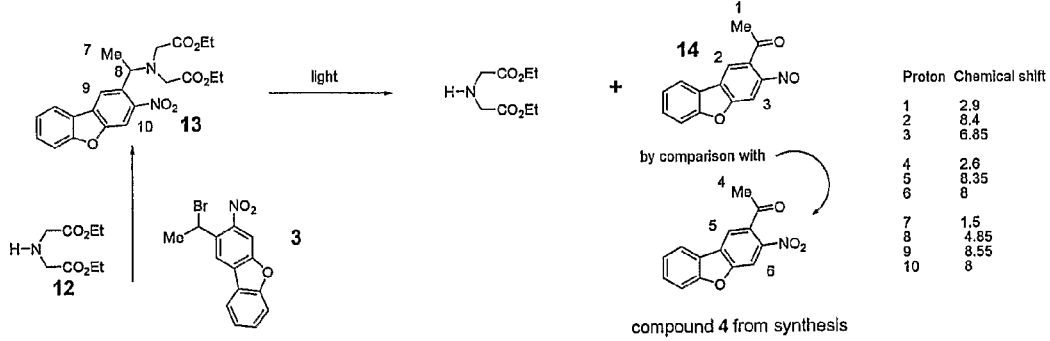
FIG. 2 is a scheme demonstrating synthesis of a NDBF-caged amine 13 from amine compound 12 and photorelease of the amine compound and DBF-nitrosoketone side product 14, as shown by NMR spectroscopy. Compound 12 can be made as described in J. Org. Chem. (1988) vol. 53, pp. 1966-9.

Synthesis of Compound 13 (FIG. 2)

Compound 3 can be obtained as shown in FIG. 3A and is depicted by formula below:

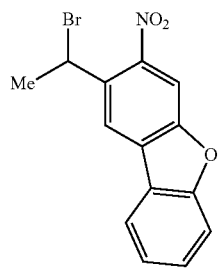

3
NDBF ethylbromide

A solution of bromide 3 (0.18 mol), amine 12 (0.3 mmol), sodium iodide (0.3 mmol) and diisoproylethylamine (0.3 mmol) was stirred at RT for 90 mins in acetonitrile. The solvent was evaporated, washed with water and ethyl acetate and purified by flash chromatography to give compound 13 (16 mg, 0.037 mmol). NMR: 8.55 (s, 1H); 8.0.5 (d, 1H, J=1.1 Hz); 8.0 (s, 1H); 7.4-7.65 (m, 3H); 4.9 (q, 1H, J=6.6 Hz); 4.09 (q, 4H, J=7 Hz); 3.6 (ABq, 4H, J=12.3 Hz); 2.6 (d, 3H, J=6.6 Hz); (t, 6H, J=7 Hz).

Example 2

Synthesis of Compound 16 (FIG. 3A)

A solution of 15 (1.24 g, 3.65 mmol) and dibutyl tin oxide (0.908 g, 3.65 mmol) in toluene (25 ml) was heated at reflux temperature for 24 h with azeotropic removal of water. The clear solution was concentrated under reduced pressure. The gummy residue obtained was stirred with CsF (0.577 g, 3.8 mmol) and bromide 3 (0.641 g, 1.4 mmol) in DMF (5 ml) at RT for 20 days. The reaction mixture was poured into water and extracted with dichloromethane (3×20 ml), dried over MgSO$_4$, filtered and evaporated using rotary evaporator. The crude product was purified by flash column chromatography (hexane:ethyl acetate, 2:1) to give 16 (0.21 g) in a yield of 21%.

$^1$H NMR (300 MHz, CDCl$_3$) δ=8.48 (s, 1H), 8.25 (s, 1H); 8.08 (d, J=1.1, 1H); 7.4-7.65 (m, 3H); 5.55 (q, 1H, J=6.6 Hz), 4.48 (dd, J=2.6, 1.3, 1H); 4.34 (t, 1H, J=8 Hz); 4-4.1 (m, 2H); 3.68 (dd, J=3.0, 0.9, 1H), 3.48 (dd, J=3.9, 2.7, 1H), 2.6 (s, 1H), 1.2-1.8 (m, 20H); 1.67 (d, 3H, J=6.6 Hz).

Example 3

Figure 4:
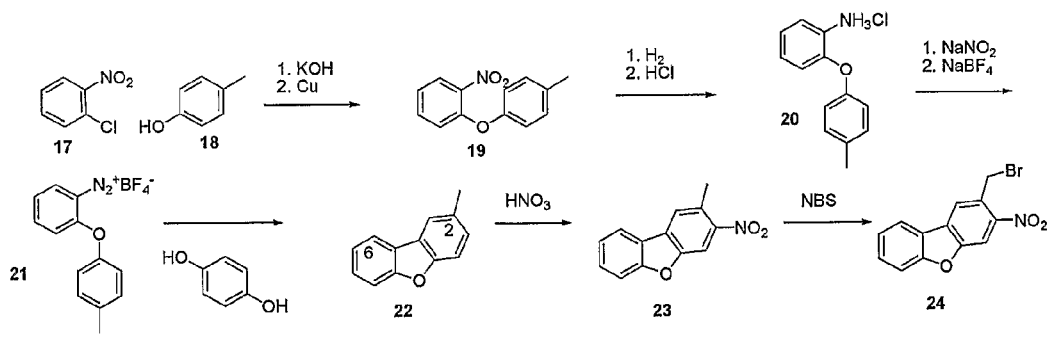
FIG. 4 is a scheme demonstrating synthesis of 2-bromomethyl-NDBF chromophore.

Synthesis of Compound 24 NDBF Methylbromide (FIGS. 4A-B)

Compound 24 NDBF methylbromide is depicted by the formula below:

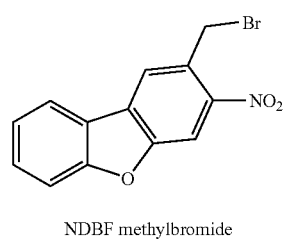

NDBF methylbromide (XXI)

Synthesis of Compound 19

Ortho-Nitrochlorobenzene (50 mmol) was coupled to para-methylphenol (69 mmol) by analogy to prior art: *Organic Syntheses Collected Vol.* 2. pp 445-446 to give 19 in 45% yield (5.12 g, 22.3 g). NMR: 7.92 (dd, 1H, J=1.8, 8 Hz); 7.47-7.35 (m, 1H); 7.15-7.2 (m, 3H); 6.9-7.02 (m, 3H); 2.35 (s 3H).

Synthesis of Compound 20

Compound 19 (22 mmol) was dissolved in ether (80 ml) with 10% Pd/C and subjected to hydrogenation at RT and atmosperic pressure until TLC showed no SM remained. The catalyst removed by filtration through Celite and the product was precipitated by bubbling HCl gas through the ether solution to give 19 as a solid in 85% yield (4.38 g, 18.6 mmol). NMR: 7.67 (dd, 1H, J=6, 1 Hz); 7.18 (dt, 1H, J=5, 1 Hz); 7.11 (d, 2H, J=7 Hz); 7.02 (d, 2H, J=7 Hz); 6.92 (dt, 1H, J=6, 0.8 Hz); 6.77 (dd, 1H, J=6, 0.8 Hz).

Synthesis of Compound 22

To a solution of 20 (2.01 g, 8.55 mmol) in water (9 ml) was added conc. HCl (3 mL). The RM was stirred vigorously and cooled with an ice bath. A solution of NaNO$_2$ (10 mmol) in water (7 mL) was added slowly, and the RM was stirred for 20 min and then filtered. A solution of NaBF4 in water was added at RT to the RM and compound 21 was isolated as a precipitate in 82% yield (2.09 g, 7.01 mmol). Compound 21 was dissolved in water (200 mL) and added to a solution of hydroquinone in water (700 mL) over 30 min. The RM was then steam distilled for 3 h, and upon cooling the product precipitated from the distillate. Compound 22 was isolated by flash chromatography (hexanes) in 48% yield (0.57 g, 3.13 mmol). NMR 7.93 (dd, 1H, J=6.2, 1.3 Hz); 7.74 (d, 1H, J=0.9 Hz); 7.55 (dd, 1H, J=7, 0.8 Hz); 7.44 (dt, 2H, J=7, 0.9 Hz); 7.34 (dd, 1H, J=6.2, 0.8 Hz); 7.27 (dd, 1H, J=7, 0.9 Hz); 2.52 (s, 3H).

Synthesis of Compound 23

To a solution of compound 22 (3.13 mmol) in trifluoroacetic acid (5 mL) was added NaNO$_3$ (0.266 g, 3.1 mmol) at RT. After 30 min the RM was poured into ice-water and the product was isolated by filtration and recrystallized from ethanol to give an orange solid (0.35 g, 1.85 mmol) in 59% yield. NMR: 8.25 (s, 1H); 7.98 (d, 1H, J=6.5 Hz); 7.87 (s, 1H); 7.61-7.57 (m, 2H); 7.41 (dt, 1H, J=1.3, 7.9 Hz); 2.76 (s, 3H).

Synthesis of Compound 24

To a solution of compound 23 (0.113 g, 0.5 mmol) in carbon tetrachloride was refluxed with N-bromosuccinamide (0.5 mmol) and benzoylperoxide (10 mg) for 4 h. Flash chromatography (10% ethyl acetate in hexanes) gave 24 (FIG. 4B) in 10% yield (14 mg, 0.05 mmol). NMR: 8.31 (s, 1H); 8.10 (s, 1H); 8.0 (d, 1H, J=0.6 Hz); 7.66-7.58 (m, 2H); 7.45 (dt, 1H, J=1.4, 6.8 Hz); 5.03 (s, 3H).

Example 4

Synthesis of Compound 26

To a solution of compound 25 (0.40 g, 1.9 mmol; made as prior art: *J. Org. Chem.* (1971) vol. 56, pp. 4671-7) in methanol (10 mL) and hydrochloric acid (2.9 mL 70% v/v) was added thallium trinitrate (1.0 g). The reaction mixture was stirred for 1 h at RT, then filtered, dissolved in water (150 mL) and dichloromethane (30 mL). Solid sodium bicarbonate was added until the pH became neutral. Flash chromatography gave 26 in a yield of 80% (1.5 mmol). NMR: 7.91 (m, 1H); 7.85 (m, 1H); 7.55 (m, 1H); 7.50 (d, 1H, J=8 Hz); 7.44 (m, 1H); 7.37-7.28 (m, 2H); 3.77 (s, 2H); 3.71 (s, 3H).

Example 5

Synthesis of Compound 27 (See FIGS. 5A-5B)

To a solution of compound 26 (0.36 g, 1.5 mmol) in trifluoroacetic acid at 4° C. was added NaNO$_3$ (1.5 mmol). After 15 min the RM was poured into water and extracted with dichloromethane to give 27 in a 20% yield.
NMR: 8.4 (s, 1H); 8.00 (m, 1H); 7.90 (s, 1H); 7.65-7.45 (m, 3H); 4.18 (s, 2H); 3.74 (s, 3H).

Example 6

Synthesis of Compound 28

Compound 28 is represented by the formula below: (XXII)

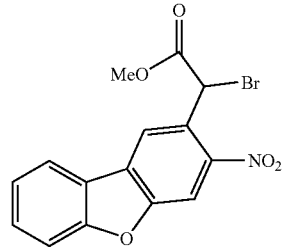

Compound 27 may be converted in compound 28 like compounds 3 and 24 using procedures described in *Proc. Natl. Acad. Sci.* (*USA*) (1994) vol. 91, pp. 8752-8756) as shown in FIG. 5.

Example 7

Figure 6:
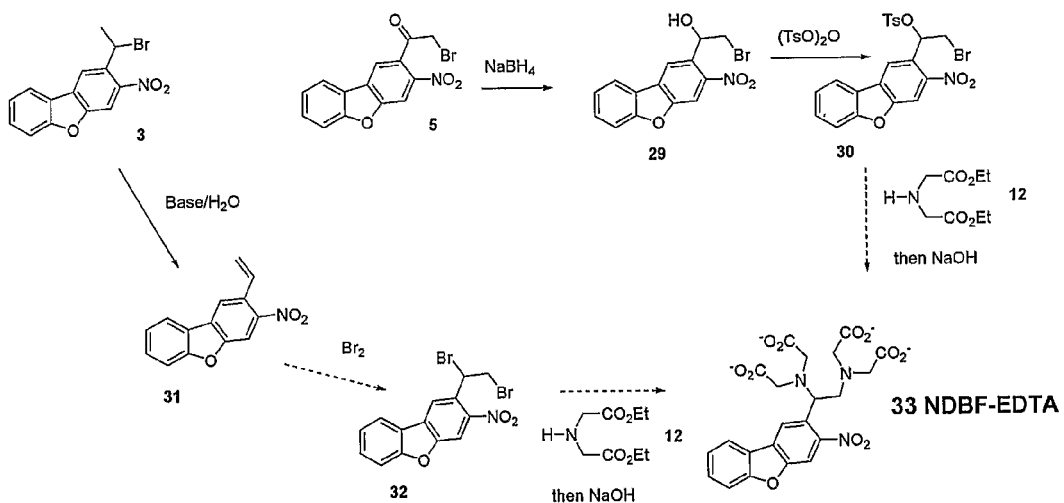
FIG. 6 is a scheme demonstrating synthesis of NDBF-EDTA.

Synthesis of Compound 29 (See FIG. 6A)

To a solution of compound 5 (10 mmol) in dioxane (75 mL) and methanol (20 mL) was added sodium borohydride (5 mmol) at RT. The reaction as quenched by addition of acetic acid (0.5 mL). Flash chromatography gave 29 in 36% yield.
NMR: 8.48 (s, 1H); 8.29 (s, 1H); 8.08 (dd, 1H, J=0.8, 1.4 Hz); 7.74-7.60 (m, 2H); 7.47 (dt, 1H, J=0.9, 6.4 Hz); 5.78 (m, 1H); 4.02 (dd, 1H, J=2.9, 11.0 Hz); 3.63 (dd, 1H, J=8.4, 10.5 Hz).

Synthesis of Compound 30

To a solution of compound 29 (0.31 g, 0.93 mmol) in pyridine (10 mL) was added to sic anhydride (1.3 g, 4 mmol) at RT. After 6 h at RT the RM was evaporated, washed with HCl (1 N), saturated sodium bicarbonate solution, and saturated salt solution. Flash chromatography with 50% dichloromethane in hexanes gave 30 in 46% yield (0.223 g).
NMR: 8.26 (s, 1H); 8.18 (s, 1H); 80.1 (m, 1H); 7.70-7.60 (m, 5H); 7.53 (m, 1H); 7.16 (d, 2H, J=8.0 Hz); 6.36 (dd, 1H, J=3.5, 7.5 Hz); 3.83 (dd, 1H, J=3.5, 10.4 Hz); 3.72 (dd, 1H, J=7.0, 11.4 Hz); 2.23 (s, 3H).

Example 8

Synthesis of Compound 34

Figure 7:
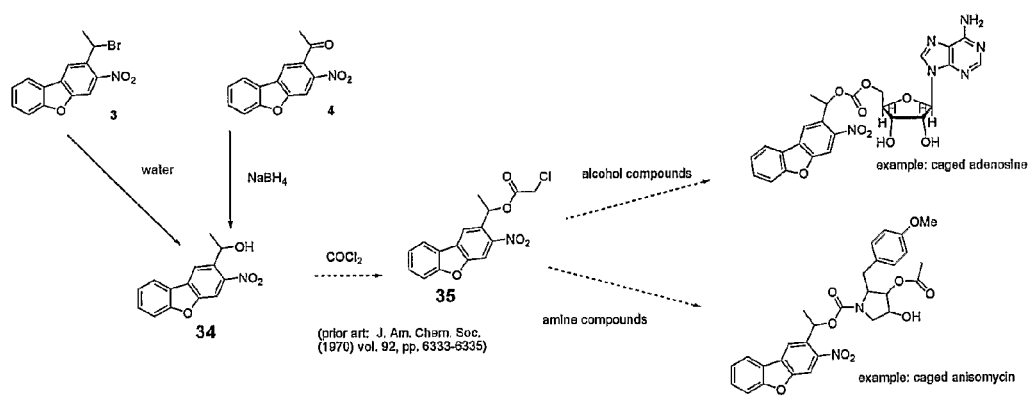
FIG. 7 is a scheme demonstrating synthesis of NDBF-oxycarbonyl amines and alcohols.

As depicted in FIG. 7, to a solution of compound 4 (0.2 mmol) in methanol (3 mL) was added sodium borohydride (0.1 mmol) to give compound 24 in 50% yield after isolation by flash chromatography with 40% dichloromethane in hexanes.
NMR: 8.39 (s, 1H); 8.15 (s, 1H); 8.01 (M, 1H); 7.61-7.54 (m, 3H); 7.42 (dt, 1H, J=1.4, 6.8 Hz); 5.67 (q, 1H, J=6.1 Hz); 1.66 (d, 3H, J=6.1 Hz).

Example 9

Synthesis of Compound 35, NBDF Oxycarbonyl Chloride (FIGS. 7A-B)

Compound 35 is represented by the formula below: (XXIII)

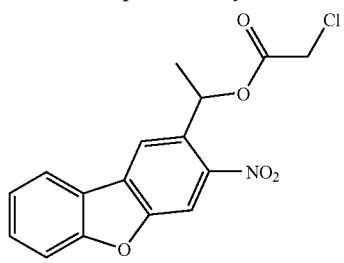

Compound 34 maybe converted into compound 35 as described by prior art (*J. Am. Chem. Soc.* (1970) vol. 92, pp. 6333-5).

Example 10

Synthesis of Caged Fluorophores

Figure 9:
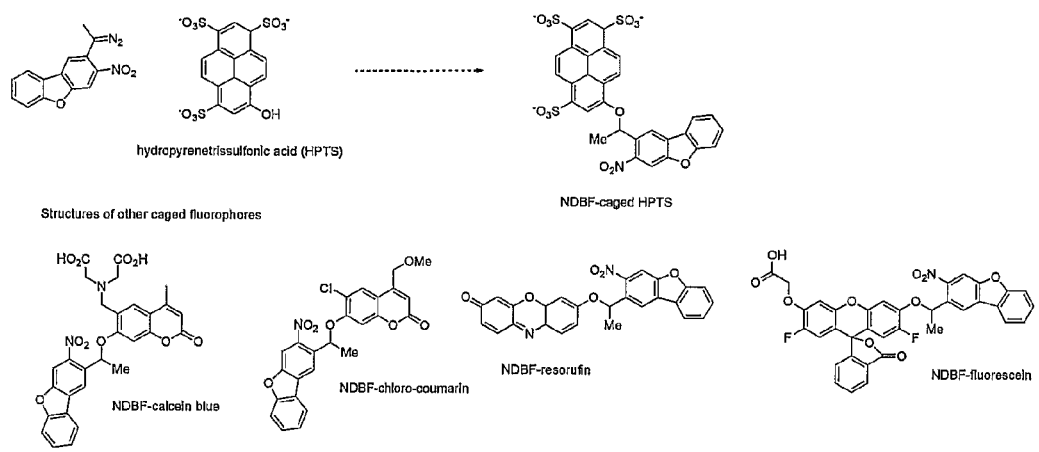
FIG. 9 is a scheme demonstrating synthesis of caged fluorophores.

A prophetic example (FIG. 9) of synthesis of NDBF-caged HPTS based upon the work by Jasuja, et al., *Biophysical Journal* (1999) vol. 76, pp. 1706-1719. The synthesis uses diazoNDBF (FIG. 8B) to cage the fluorophore. The same chemistry can be used for many other similar molecules, each having a phenol functionality.

Example 11

FIG. 10 is a scheme demonstrating synthesis of caged glutamate.

A prophetic example (FIG. 9) of the synthesis of NDBFindolinyl-glutamate, using chemistry already developed for 2-bromomethyl-3-nitrodibenzofuran (FIG. 4; compound 24) and MNI-glutamate (Matsuzaki, et al., 1999). Thus, we will couple the commercially available 4-hydroxyindole and 2-chloronitrobenzene, the product of this reaction will be reduced to its amine, which can then be diazotized and the dibenzofuran will be produced by reductive ring closure in the presence of hydroquinone to give the dibenzofuranindole. This indole will be reduced to its indoline with sodium cyanoborohydride, then coupled to protected glutamate. The final two steps in the synthesis will be nitration and deprotection with trifluoroacetic acid, in a synthetic sequence we have previously used for MNI-glutamate (Matsuzaki, et al., 1999).

While the invention has been described in detail and with reference to specific examples thereof, it will be apparent to one skilled in the art that various changes and modifications can be made therein without departing from the spirit and scope thereof.

REFERENCES

G. C. R. Ellis-Davies, (2005) in *Imaging In Neuroscience and Development* (Eds.: R. Yuste, A. Konnerth), Cold Spring Harbor Laboratory Press, Cold Spring Harbor, 2005, 367-374.

Corrie, J. E. T. and Trentham, D. R. (1993) "Caged nucleotides and neurotransmitters" In *Bioorganic Photochemistry* 2 (ed. H. Morrison) John Wiley and Son, New York, pp. 243-305.

Corrie JET, (2005) "Photoremovable Protecting Groups Used for the Caging of Biomolecules" in Dynamic Studies in Biology (eds Maurice Goeldner (Editor), Richard Givens) Wiley.

G. C. R. Ellis-Davies and J. H. Kaplan, "Synthesis of Photolabile Chelators for Multivalent Cations." U.S. Pat. No. 4,981,985

G. C. R. Ellis-Davies and J. H. Kaplan, "Structure and Synthesis of Nitrophenyl-EGTA, a Caged Calcium, Intermediates Thereof and a Method of Producing a High Photochemical Yield of Liberated Calcium." U.S. Pat. No. 5,498,765

Ellis-Davies, G. C. R. and Kaplan, J. H. (1994) "Nitrophenyl-EGTA, a photolabile chelator that selectively binds $Ca^{2+}$ with high affinity and releases it rapidly upon photolysis" *Proc. Natl. Acad. Sci. USA*, 91: 187-191.

G. C. R. Ellis-Davies, J. H. Kaplan, J. H. A new class of photolabile chelators for the rapid release of divalent cations: generation of caged Ca and caged Mg. *J. Org. Chem.* 53 (1988) 1966-1969.

R. Jasuja, J Keyoung, G P Reid, D R Trentham, S Khan. Chemotactic responses of *Escherichia coli* to small jumps of photoreleased L-aspartate. *Biophysical Journal* (1999) vol. 76, pp. 1706-1719.

J. H. Kaplan, G. C. R. Ellis-Davies, Photolabile chelators for the rapid photorelease of divalent cations Proc. Natl. Acad. Sci. (USA) 85 (1988) 6571-6575.

G. C. R. Ellis-Davies, Synthesis of photolabile EGTA derivatives. Tetrahedron Lett. 39 (1998) 953-957.

M. Matsuzaki, A. Tachikawa, G. C. R. Ellis-Davies, Y. Miyashita, M. Iino and H. Kasai "Dendritic spine morphology is critical for AMPA receptor expression in hippocampal CA1 pyramidal neurons" *Nature Neuroscience* 2001, 4, 1086-1092.

S. R. Adams, V. Lev-Ram, R. Y. Tsien, A new caged $Ca^{2+}$, azid-1, is far more photosensitive than nitrobenzyl-based chelators. Chem & Biol. 4 (1997) 867-878.

R. Y. Tsien, R. S. Zucker, Control of cytoplasmic calcium with photoabile tetracaroxylate 2-nitrobenhydrol chelators. Biophys. J. 50 (1986) 843-853.

S. R. Adams, J. P. Y. Kao, G. Grynkiewicz, A. Minta, R. Y. Tsien, R. Y. Biologically useful chelators that release $Ca^{2+}$ upon illumination. J. Am. Chem. Soc. 110 (1998) 3212-3220.

S. Kantevari, M. Egger, C. Hoing, E. Niggli, and G. C. R. Ellis-Davies "Synthesis and 2-photon photolysis of 6-(ortho-nitroveratryl)-caged $IP_3$." ChemBioChem. 2006, 7, 174-182.

Engert, F, Paulus, G. G., and Bonhoeffer, T. (1996) "A low cost UV laser for flash photolysis of caged compounds" *J. Neurosci. Methods.* 66, 47-54.

Engels, J. & Schlaeger, E.-J. Synthesis, structure and reactivity of adenosine cyclic 3',5'-phosphate benzyl triesters. *J. Med. Chem.* 20, 907-911 (1977).

Wieboldt, R., Gee, K. Y., Niu, L., Ramash, D., Carpenter, B. K., and Hess, G. P. (1994b) "Photolabile presurors of glutamate: Synthesis, photochemical properties, activation of glutamate receptors in the microsecond time scale."*Proc. Natl. Acad. Sci. (USA)* (1994) vol. 91, pp. 8752-8756)

Chromophore Containing Structures

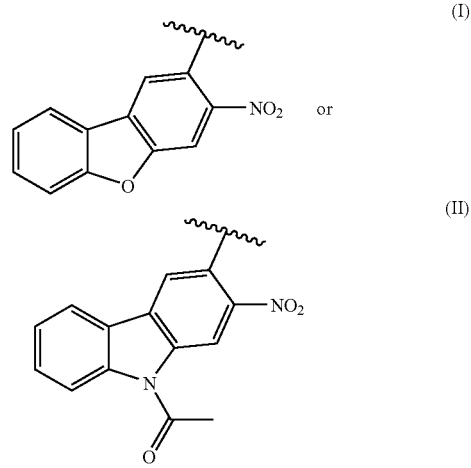

Derivatives of the chromophore of the invention can be made by substitutions of hydrogen in any position of a benzyl ring, for example, as depicted by the following formula

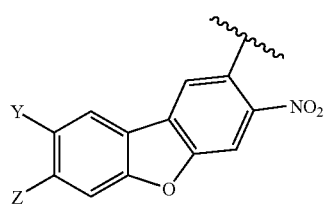
(III)
wherein Y=H, OMe, OEt, OPr, O(CH$_2$)$_n$CO$_2$H, (CH$_2$)$_n$CO$_2$H and Z=H, OMe, OEt, OPr, O(CH$_2$)$_n$CO$_2$H, (CH$_2$)$_n$CO$_2$H; or
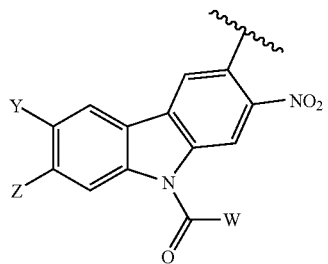
(IIIA)
wherein W=H, Me, Et, Pr, CO$_2$H, (CH$_2$)$_n$CO$_2$H, CH$_2$, CHMe, CMe$_2$, (CH$_2$)$_n$PO$_3$H$_2$, (CH$_2$)$_n$SO$_3$H.
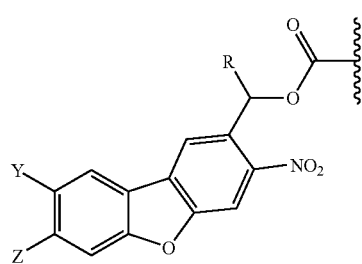
(IV)
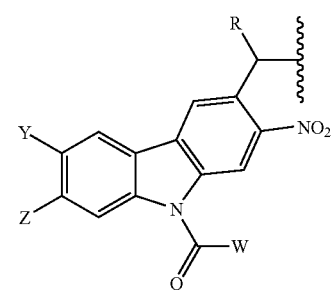
(V)
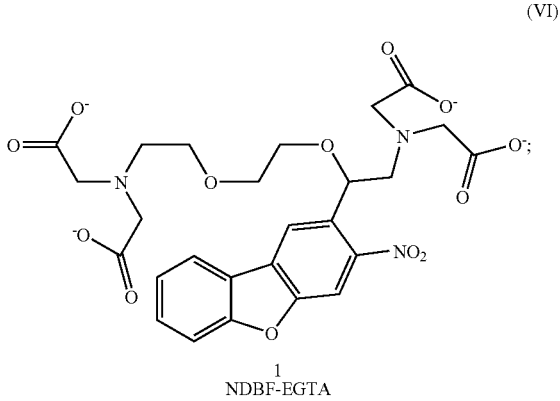
(VI)
1
NDBF-EGTA
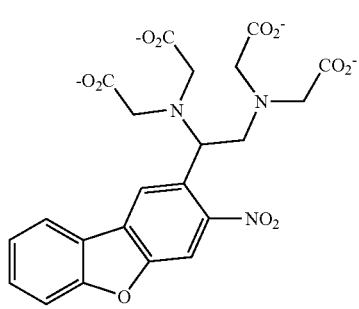
(VII)
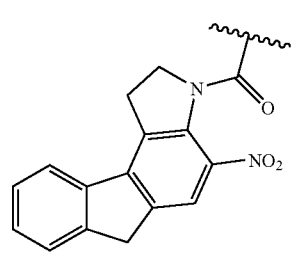
(VIII)
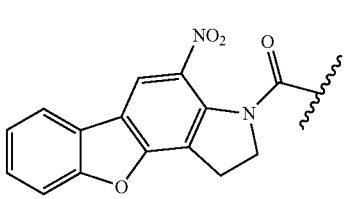
(IX)
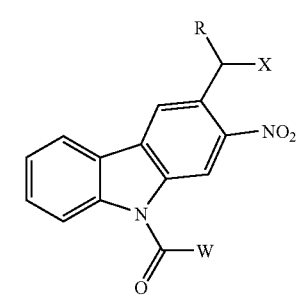
(X)
wherein W=H, Me, Et, Pr, CO$_2$H, (CH$_2$)$_n$CO$_2$H, CH$_2$, CHMe, CMe$_2$, (CH$_2$)$_n$PO$_3$H$_2$, (CH$_2$)$_n$SO$_3$H; R=H or Me, and n is an integral if 0 to 10;
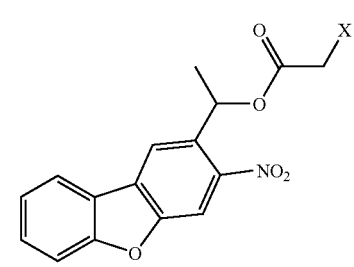
(XI)

(XIA)
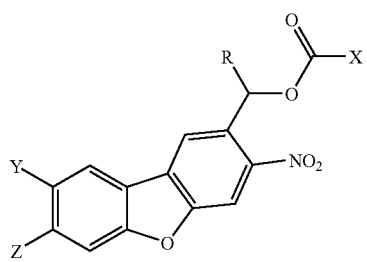
R=H, Me, Et, Pr, $CO_2H$, $(CH_2)_nCO_2H$, $COH_2$, COHMe, $COMe_2$, $(CH_2)_nPO_3H_2$, $(CH_2)_nSO_3H_2$.
Y=H, OMe, OEt, OPr, $O(CH2)_nCO2H$, $(CH2)_nCO2H$
Z=H, OMe, OEt, OPr, $O(CH2)_nCO2H$, $(CH2)_nCO2H$
X=caged substrate
(XII)
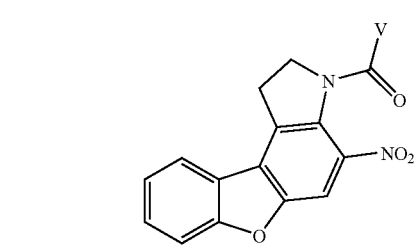
(XIII)
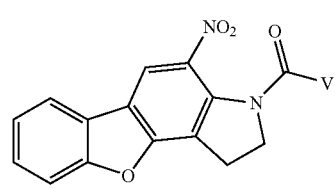
(XIV)
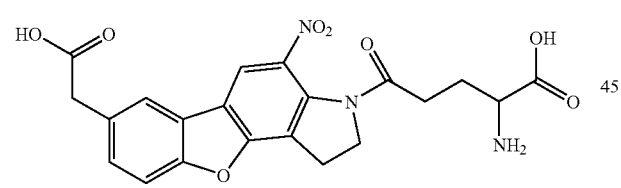
(XV)
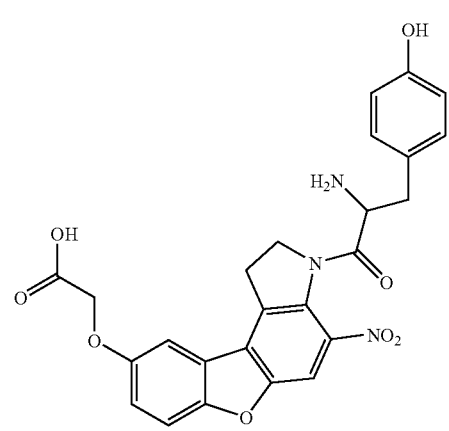
(XVI)
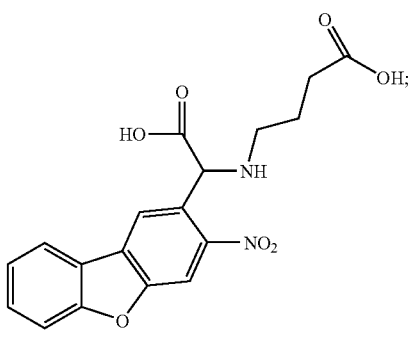
N-caged cNDBF-gaba
(XVII)
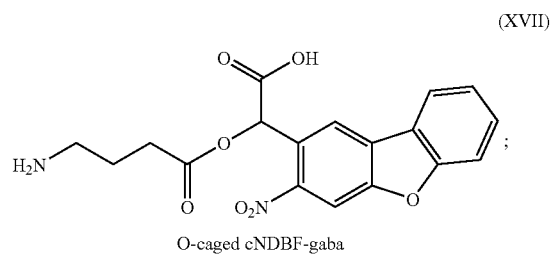
O-caged cNDBF-gaba
(XVIII)
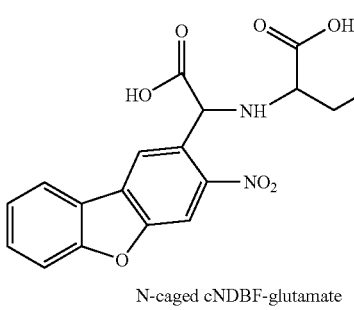
N-caged cNDBF-glutamate
and
(XIX)
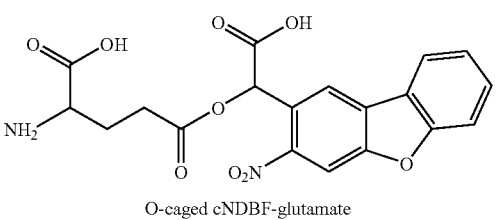
O-caged cNDBF-glutamate
(XX)
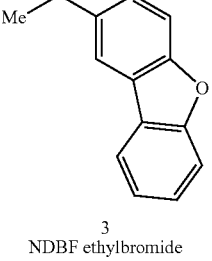
3
NDBF ethylbromide -continued
(XXI)
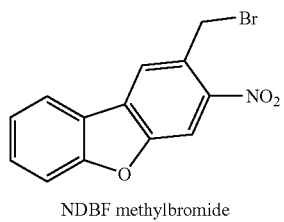
NDBF methylbromide
(XXII)
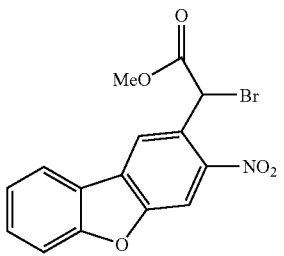
(XXIII)
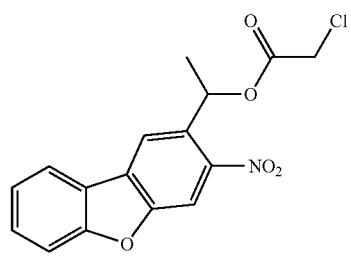
(XXIV)
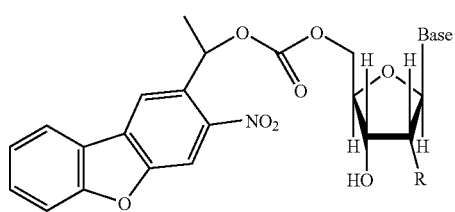
wherein R=OH or H; base=adenine, guanine, thymine, cytosine
(XXV)
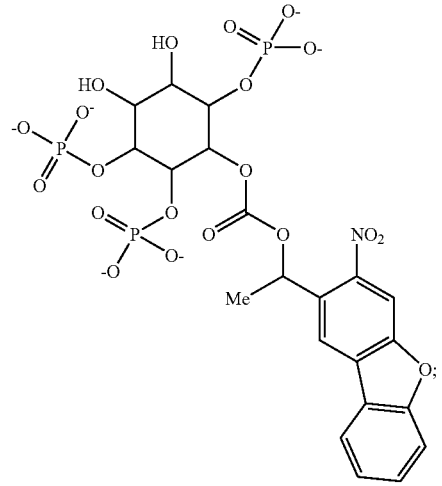
6-NBDF-IP3
(XXVI)
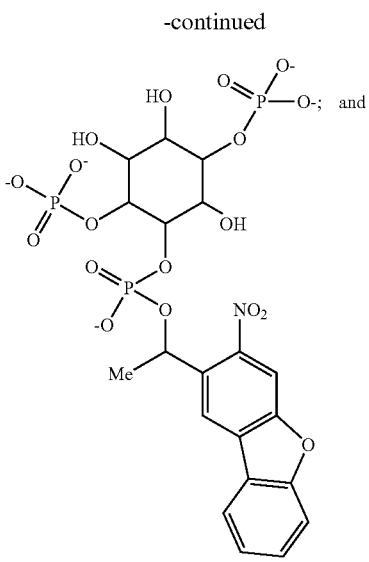
5-NDBF-IP3
(XXVII)
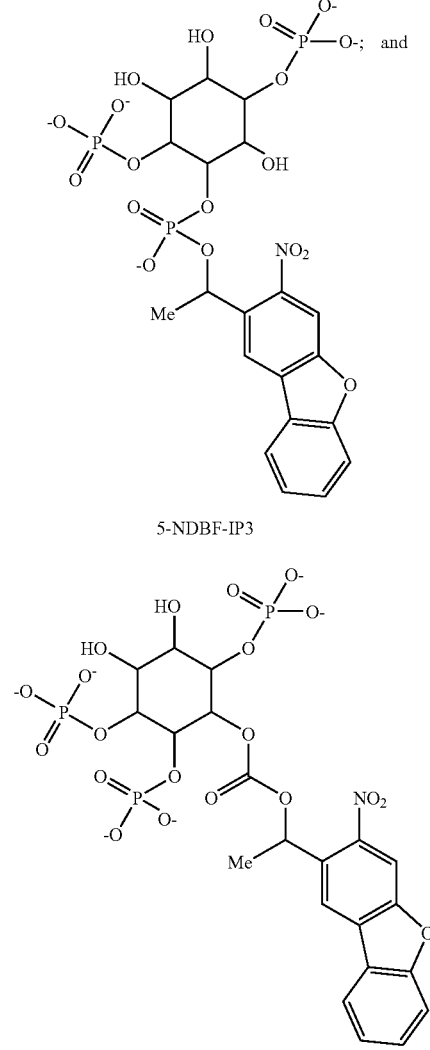
6-NBDFoxcarbonyl-IP3
(XXVIII)
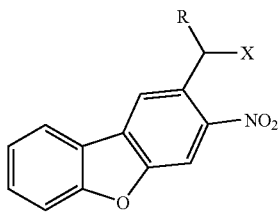
R=H, Me, Et, Pr, OMe, OEt, OPr, O(CH$_2$)$_n$CO$_2$H, (CH$_2$)$_n$CO$_2$H; (CH$_2$)$_n$SO$_2$H; (CH$_2$)$_n$PO$_3$H$_2$
(XXIX)
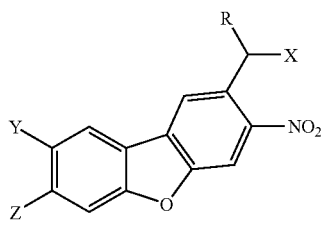

What is claimed is:

1. A photolabile compound represented by one of the following formulas:

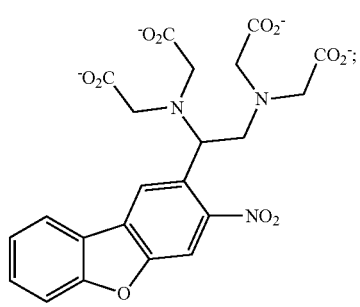
(VII)

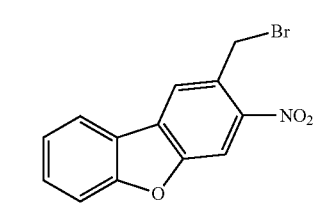
(XXI)

NDBF methylbromide;

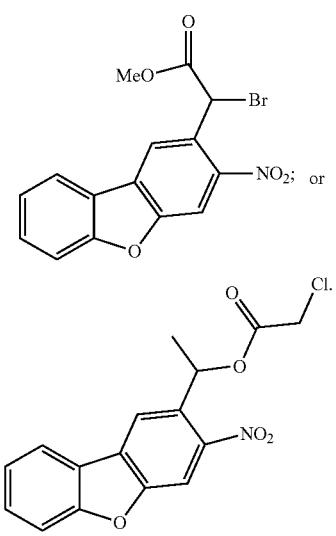
(XXII)

(XXIII)

2. A photolabile compound represented by one of the following formulas:

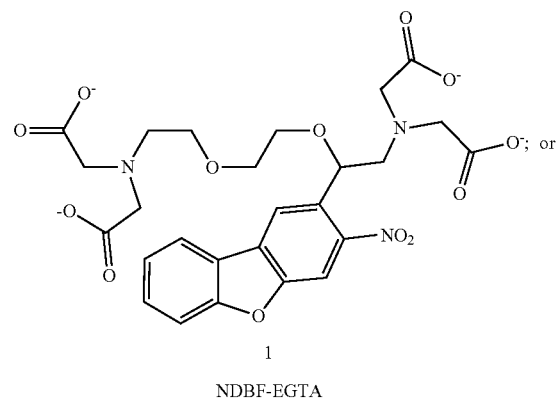
(VI)

NDBF-EGTA

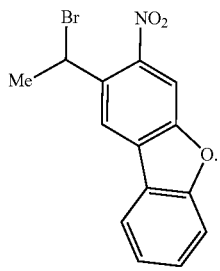
(XX)

NDBF ethylbromide

3. A photolabile compound represented by one of the following formulas:

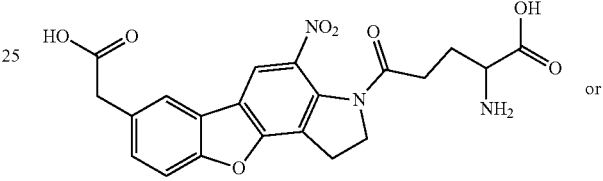
(XIV)

or

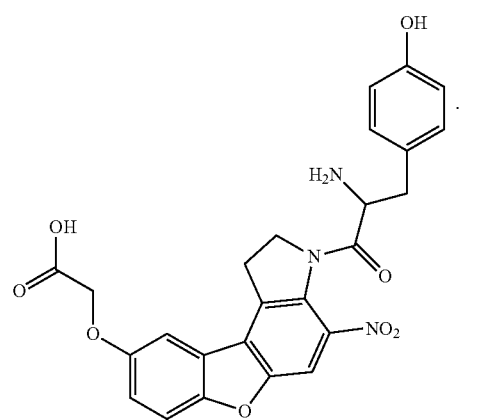
(XV)

4. A photolabile compound represented by one of the following formulas:

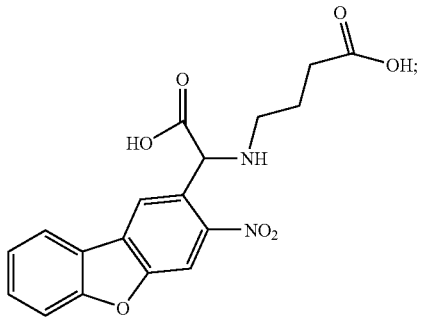
(XVI)

N-caged cNDBF-gaba

-continued

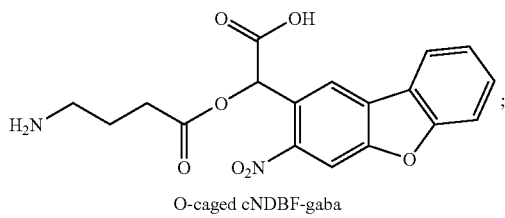

O-caged cNDBF-gaba (XVII)

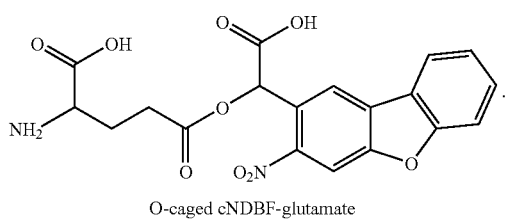

N-caged cNDBF-glutamate (XVIII)

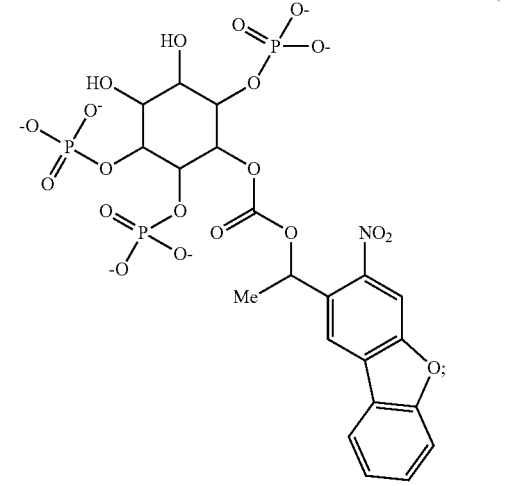

O-caged cNDBF-glutamate (XIX)

5. A photolabile compound represented by one of the following formulas:

(XXV)

6-NBDF-IP3

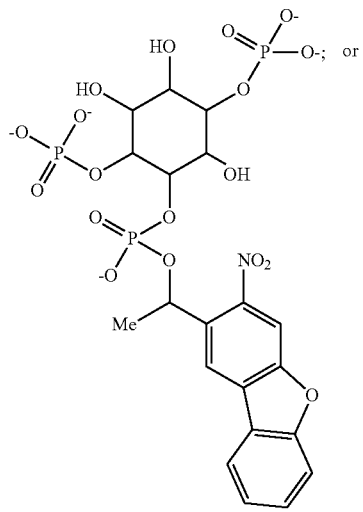

5-NDBF-IP3 (XXVI)

6-NBDFoxcarbonyl-IP3 (XXVII)

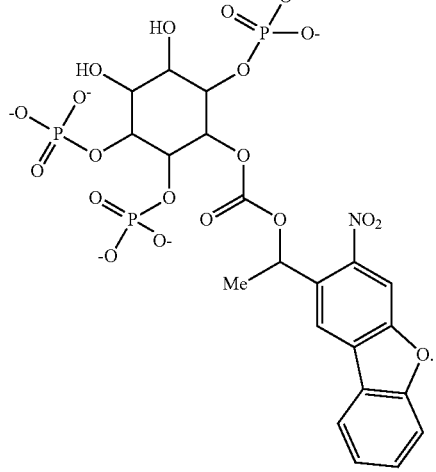

6. A method of photochemical release of an effector molecule from a caged compound, the method comprising:
   (a) providing a photolabile compound of claim 4; and
   (b) photolyzing the photolabile compound with light to release the effector molecule, wherein the effector molecule is selected from gamma-aminobutyric acid and glutamate.

* * * * *